US011419601B2

(12) United States Patent
Krespi et al.

(10) Patent No.: US 11,419,601 B2
(45) Date of Patent: Aug. 23, 2022

(54) DEVICE AND METHODS FOR USE IN ROBOTIC ASSISTED SURGERY FOR TREATMENT OF OBSTRUCTIVE SLEEP APNEA

(71) Applicants: Yosef Krespi, New York, NY (US); Ron Hadani, Herzeliya (IL)

(72) Inventors: Yosef Krespi, New York, NY (US); Ron Hadani, Herzeliya (IL)

( * ) Notice: Subject to any disclaimer, the term of this patent is extended or adjusted under 35 U.S.C. 154(b) by 329 days.

(21) Appl. No.: 15/912,517

(22) Filed: Mar. 5, 2018

(65) Prior Publication Data

US 2018/0280016 A1    Oct. 4, 2018

Related U.S. Application Data

(60) Provisional application No. 62/466,491, filed on Mar. 3, 2017.

(51) Int. Cl.
| | | |
|---|---|---|
| *A61B 17/04* | (2006.01) | |
| *A61B 17/29* | (2006.01) | |
| *A61B 17/06* | (2006.01) | |
| *A61B 34/30* | (2016.01) | |
| *A61B 90/00* | (2016.01) | |
| *A61B 34/20* | (2016.01) | |
| *A61B 17/24* | (2006.01) | |

(52) U.S. Cl.
CPC ...... *A61B 17/0469* (2013.01); *A61B 17/0483* (2013.01); *A61B 17/06109* (2013.01); *A61B 17/29* (2013.01); *A61B 17/0485* (2013.01); *A61B 34/30* (2016.02); *A61B 90/361* (2016.02); *A61B 2017/0608* (2013.01); *A61B 2017/06042* (2013.01); *A61B 2017/06176* (2013.01); *A61B 2017/248* (2013.01); *A61B 2034/2057* (2016.02); *A61B 2090/373* (2016.02)

(58) Field of Classification Search
CPC ............ A61B 17/0469; A61B 17/0483; A61B 17/0485; A61B 17/06; A61B 17/29; A61B 34/30; A61B 2017/248; A61F 5/566
See application file for complete search history.

(56) References Cited

U.S. PATENT DOCUMENTS

| | | | | |
|---|---|---|---|---|
| 5,337,736 | A | * | 8/1994 | Reddy ................ A61B 17/0218 128/898 |
| 6,099,538 | A | * | 8/2000 | Moses ................ A61B 17/0469 606/139 |

(Continued)

*Primary Examiner* — Diane D Yabut
*Assistant Examiner* — Christina C Lauer
(74) *Attorney, Agent, or Firm* — Joseph P. Aiena

(57) ABSTRACT

There is provided a suture passer device used in procedures of robotic assisted minimally invasive suspension of the hyoid and tongue base in treatment of sleep apnea. The suture passer device is a dual use suture passer, having both suture insertor and extractor functionality on a single unitary instrument section of the device by means of insertion and extraction hooks positioned on an elongated needlelike body which is connected to a handle grip. The insertion and extraction hooks receive a suture via an opening in the body of the instrument, with the suture capable of removal and fastening to the extraction hook by robotic forceps. Procedures for using the device are disclosed which include a single point of entry on a patient and the device moved to first and second positions above and below the hyoid bone during robotic assisted surgery.

24 Claims, 27 Drawing Sheets

(56) References Cited

U.S. PATENT DOCUMENTS

| | | | | |
|---|---|---|---|---|
| 6,723,107 B1* | 4/2004 | Skiba | ............... | A61B 17/0469 |
| | | | | 606/144 |
| 2005/0021055 A1* | 1/2005 | Toubia | ............... | A61B 17/0057 |
| | | | | 606/144 |
| 2007/0137655 A1* | 6/2007 | Paraschac | ............... | A61F 5/56 |
| | | | | 128/848 |
| 2011/0245850 A1* | 10/2011 | van der Burg | ..... | A61B 17/0401 |
| | | | | 606/145 |
| 2013/0074849 A1* | 3/2013 | Rousseau | ............... | A61B 17/06 |
| | | | | 128/848 |
| 2013/0139828 A1* | 6/2013 | Rousseau | ........... | A61B 17/0642 |
| | | | | 128/848 |
| 2013/0150871 A1* | 6/2013 | Belson | ............. | A61B 17/00234 |
| | | | | 606/148 |
| 2015/0250476 A1* | 9/2015 | Feezor | ............ | A61B 17/06166 |
| | | | | 606/144 |

* cited by examiner

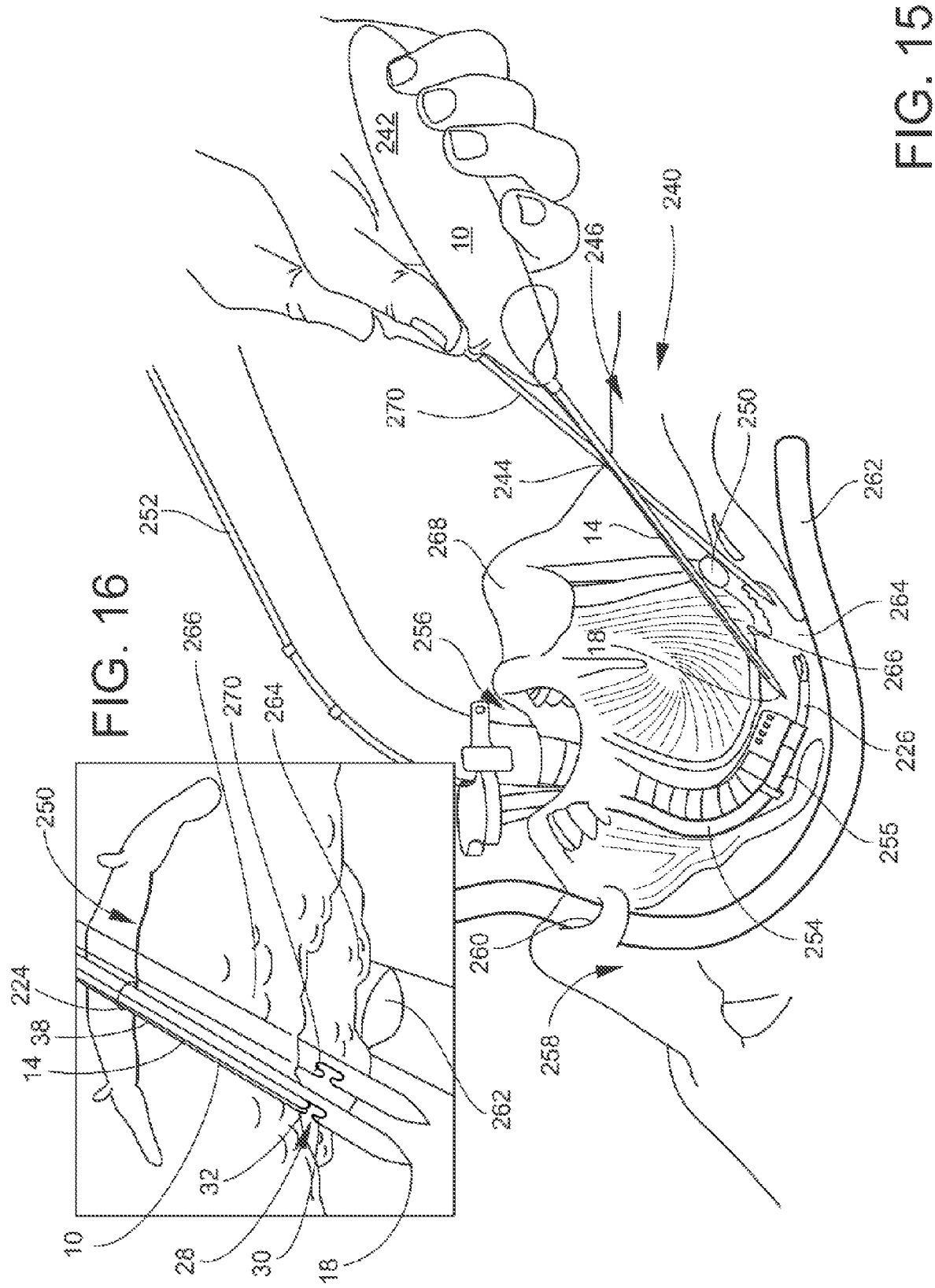

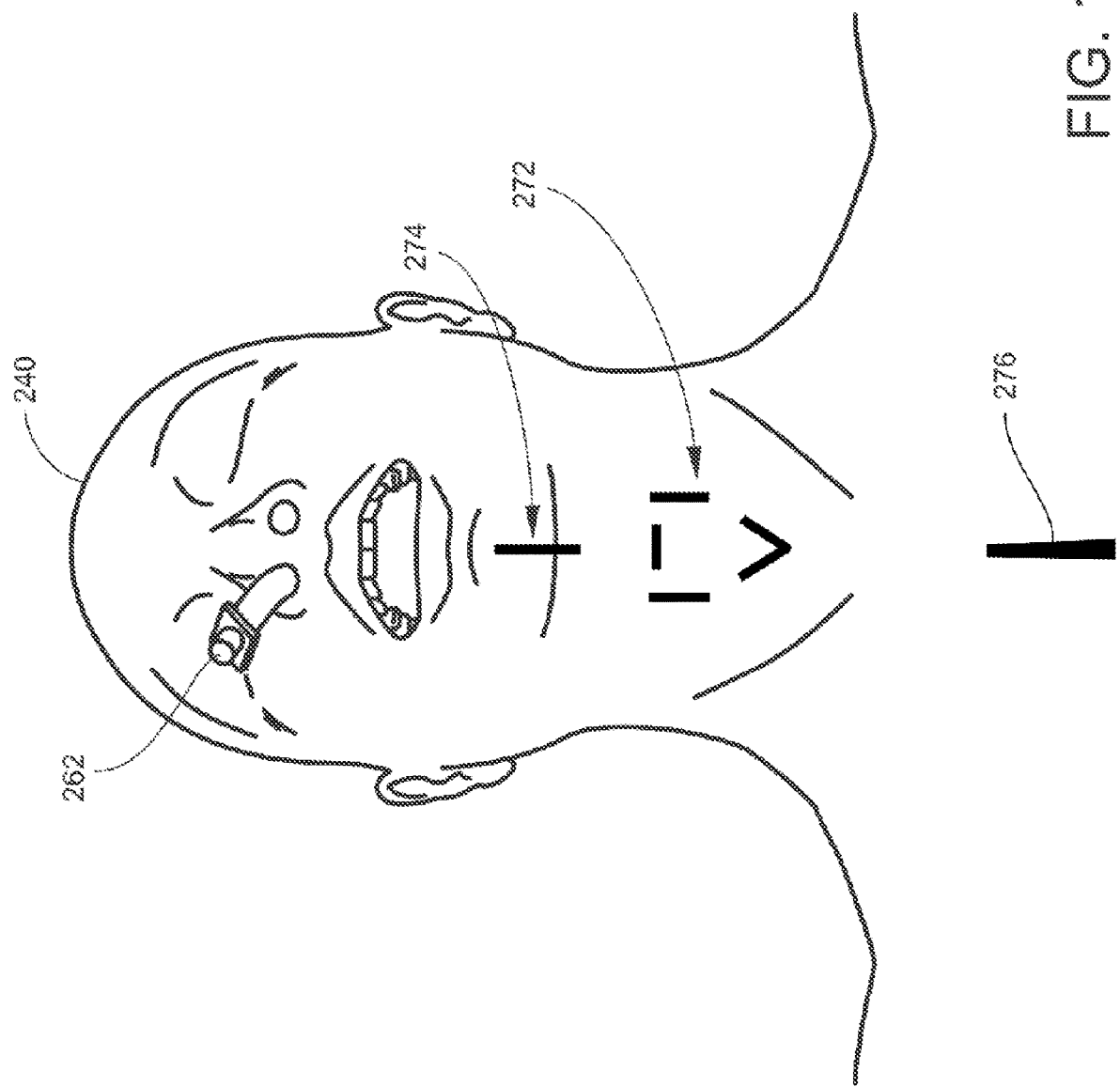

DEVICE AND METHODS FOR USE IN ROBOTIC ASSISTED SURGERY FOR TREATMENT OF OBSTRUCTIVE SLEEP APNEA

CROSS REFERENCE TO RELATED APPLICATIONS

This application claims benefit of and priority to U.S. Provisional Application Ser. No. 62/466,491 filed on Mar. 3, 2017, and which is incorporated by reference herein in its entirety.

FIELD OF THE INVENTION

The present invention relates to a suture passer device for use in robotic assisted surgery in the treatment of obstructive sleep apnea and methods of using the device.

BACKGROUND

Obstructive sleep apnea (OSA) is a well-known problem. Sleep disorders cost both people and corporations financially in lost productivity and apnea has similar risk factors for heart disease as other known problems such as smoking, high cholesterol and alcohol. OSA is a disruption of more than 10 seconds between breaths during sleep with more than 10 episodes per hour. With hypertension patients, 5 episodes per hour may be defined as OSA.

OSA is a large and growing problem worldwide and is an increasing problem with correlations to overweight and obesity as well as increasing age. It is also associated with expensive medical care, including post-surgical and post-procedural complications and longer hospital stays.

When OSA is diagnosed, treatment is often prescribed on four levels of ascending complexity: a.) behavioral changes, weight loss or modified drinking, smoking or sleeping habits; b.) CPAP pump and mask to assist in sleep breathing; c.) oral appliances if CPAP is not tolerated by the patient; and d.) surgical procedures if the above are not successful.

The common surgical procedures for OSA include nasal surgery such as septum, turbinate reduction, swell bodies; oro-pharyngeal; and tongue base which includes tongue reduction, hypoglossal nerve stimulation, and hyoid suspension. Prior tongue and hyoid suspension and expansion surgical techniques have been invasive surgeries. The procedures typically require more than one surgical entry point on a patient and provide little maneuverability and visibility for the surgeon during the process for handling the sutures needed to suspend the tongue and hyoid.

SUMMARY

The present invention is a suture passer device used in procedures of robotic assisted minimally invasive suspension of the hyoid. The suture passer device of the present invention is a dual use suture passer, having both suture insertor and extractor functionality on a single unitary device. That is, insertion and extraction are all performed with one instrument on the device of the present invention. The suture passer device of the present invention is a static needle with two directional hooks to achieve insertion and extraction under robotic visualization. This is accomplished without any spring mechanism to catch the suture and also without changing the diameter of the instrument (ie. an alligator tip).

The suture passer device of the present invention includes an elongated needle like instrument having a body with an external surface, a first end received by a handle section and a second end with a needle tip. The instrument has an insertion hook for securing and delivering a suture during insertion and also an extraction hook for receiving and securing a suture during extraction. The insertion hook and the extraction hook are defined by an open mouth area located between the insertion hook and the extraction hook, and an internal surface extending from the external surface of the body adjacent to the insertion hook to the external surface of the body adjacent to the extraction hook, thereby forming an opening in the body of the suture passer device which receives the suture when the suture is placed into the mouth area on the instrument. The insertion hook receives and secures the suture for delivery of an insertion of the suture by the instrument and the extraction hook receives and secures the suture for extraction of the suture during extraction by the instrument. The suture passer device includes a head section angled away from a central axis of the instrument body of the device. The body of the instrument has a cylindrical or oval shape, but other shapes are within the scope of the present invention.

With the suture passer device of the present invention the insertion hook is located on the instrument body at a position proximal to the handle section relative to the extraction hook.

The suture passer device of the present invention allows for an alternative to tongue based surgery. The procedure with the device of the present invention provides for robotic guided surgery with improved accuracy, reach and visualization in the surgical area.

The procedure is facilitated by the dual use suture passer (insertor-extractor) device of the present invention and includes use of barbed sutures. There is also a special design tongue blade for exposure and safety. The suspension of tissue is powered by special barbed sutures, composed of an absorbable material. With the device and procedure of the present invention, there are no external (skin) or internal (mucosal) incisions and the procedure is performed with the central safe zone of the patient's neck.

The surgical time is less than one hour and results in minimal post-surgical pain or discomfort. Recovery is speedy and same day oral diet is achieved. There are no restrictions for post-op CPAP use, when indicted by the medical professional. The procedure can be combined with lingual tonsil ablation (laser, coblation, RF, cautery).

BRIEF DESCRIPTION OF THE DRAWINGS

Some embodiments of the invention, and of making and using the invention, as well as the best mode contemplated of carrying out the invention, are described in detail below, by way of example, with reference to the accompanying drawings, in which like reference characters designate like elements throughout the several views, and in which:

FIG. 15 is cross sectional view of a patient having robot assisted surgery with the suture passer device of the present invention;

FIG. 16 is a view of the internal surgical area of the patient with the suture passer device of the present invention in first and second positions;

FIG. 17 is an illustration which indicates the safe-zone for a patient to receive the suture passer during surgery;

DETAILED DESCRIPTION

Figure 1:
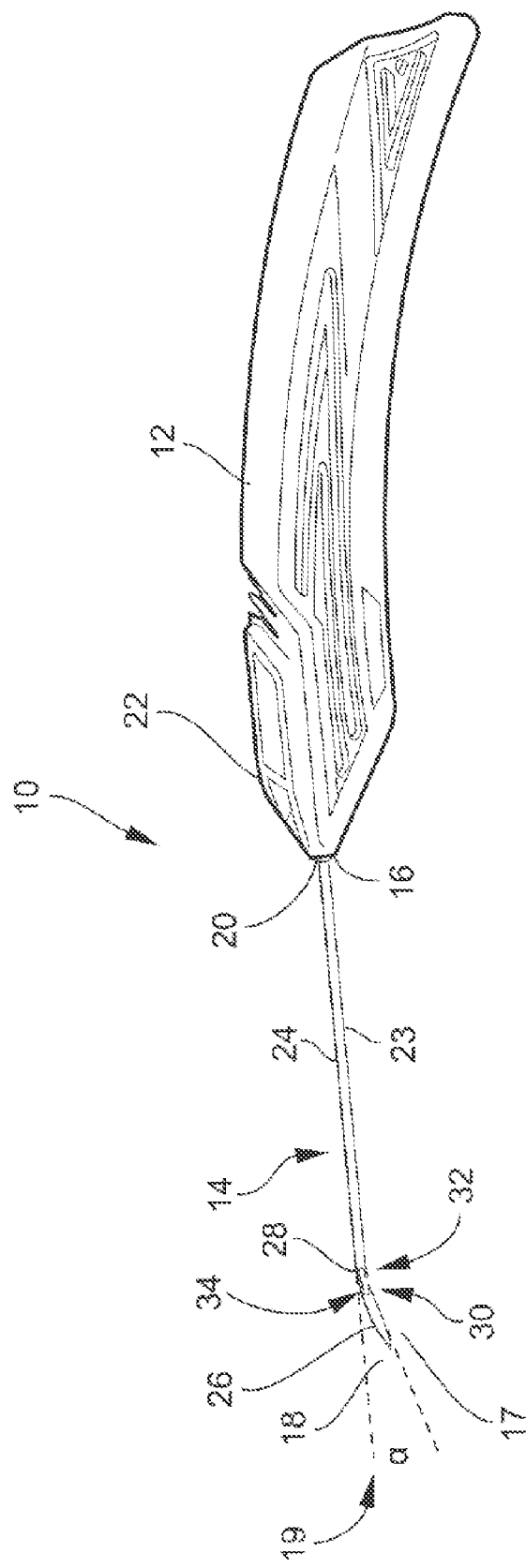
FIG. 1 is an illustration of the device of the present invention.

With reference to the Figures, the present invention is herein described. FIG. 1 illustrates the suture passer device 10 of the present invention, which has both inserter and extraction features and capability in a unitary instrument piece. The present invention includes an elongated needle-like passer instrument 14 fastened to a handle grip 12 which receives a first end 16 of the passer instrument 14. A fastener 20 secures the passer instrument 14 to the handle grip 12. A stabilizer piece 22 located inside the handle grip 12 can connect the first end 16 of the instrument 14 by receiving the instrument 16 through the fastener 20. The second end 17 of the passer instrument 14 has a needle tip 18. The solid rigid elongated needle like passer 14 has a smooth surface 24, and preferably a cylindrical shaped body 23, although other shapes which include flat edges are included within the scope. The needlelike passer instrument 14 and tip 18 are of sufficient strength to withstand potential impact with hard tissue, such as bone, or metal instruments when used in surgical procedures. The head section 26 of the passer instrument is positioned at an angle away from the central axis 19 of the instrument 14. On the surface 24 of the instrument 14, positioned at or in proximity to the head section 26 is a mouth 28 which defines an opening 34 within the body 23 of the instrument 14. The opening 34 is carved or formed out of the instrument 14 and a continuous internal surface 36 which extends from the mouth 28. The opening 34, surface 36 and mouth area 38 create at least one distal hook 30 and at least proximal hook 32. With the device 10 of the present invention, the extractor hook 30 is located at a distal position and used as an extractor for a suture 38 and the insertion hook 32 is located at a proximal position and used as the inserter for a suture 38.

Figure 2:
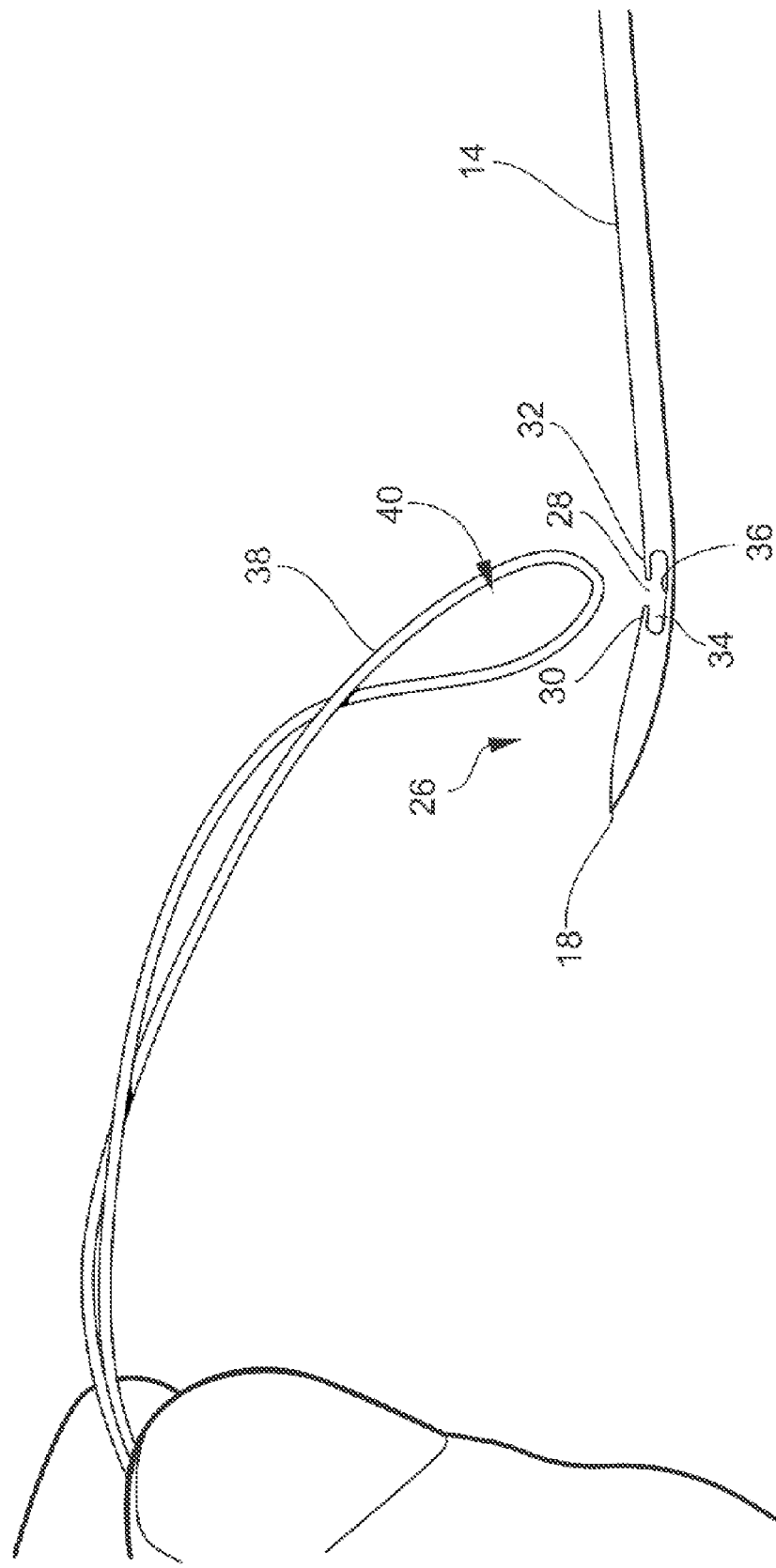
FIG. 2 is an illustration of the device of the present invention receiving a suture.

FIG. 2 illustrates a close up of the head section 26, instrument 14 and hooks 30 and 32 of the suture passer device 10 of the present invention. A loop 40 of suture 38 is shown in a figure of eight type shape. The suture 38 is placed into the mouth 28 of the instrument 14 and looped under insertion hook 32 and can be tightened in place by the medical professional. This "loads" the suture passer 10 and it is ready for use in a medical procedure. The suture 38 is inserted into a patient as the suture passer 10 is inserted. After insertion of the suture 38, the suture passer 10 needs to extract the suture 38 in order to form a stitch or loop of suture between an insertion point and an extraction point. For the extraction function of the device 10, the suture 38 is removed from insertion hook 32 and placed under extraction hook 30. By applying a pulling force on the device 10 of the present invention, the suture 38 is pulled by the extraction hook 30 in the same direction with the device 10 and may exit the patient or be brought to a desired position. The insertion hook 32 and extraction hook 30 may be different dimensions or the same, as long as each hook 30 and 32 is capable of receiving and holding the suture 38.

It should be noted that one or both of the hooks 30 and 32 and/or the area near the hooks 30 or 32 can be marked or color coded 42 to visually aid the surgeon in distinguishing an extraction hook 30 from an insertion hook 32 during the surgical procedure.

Figure 3:
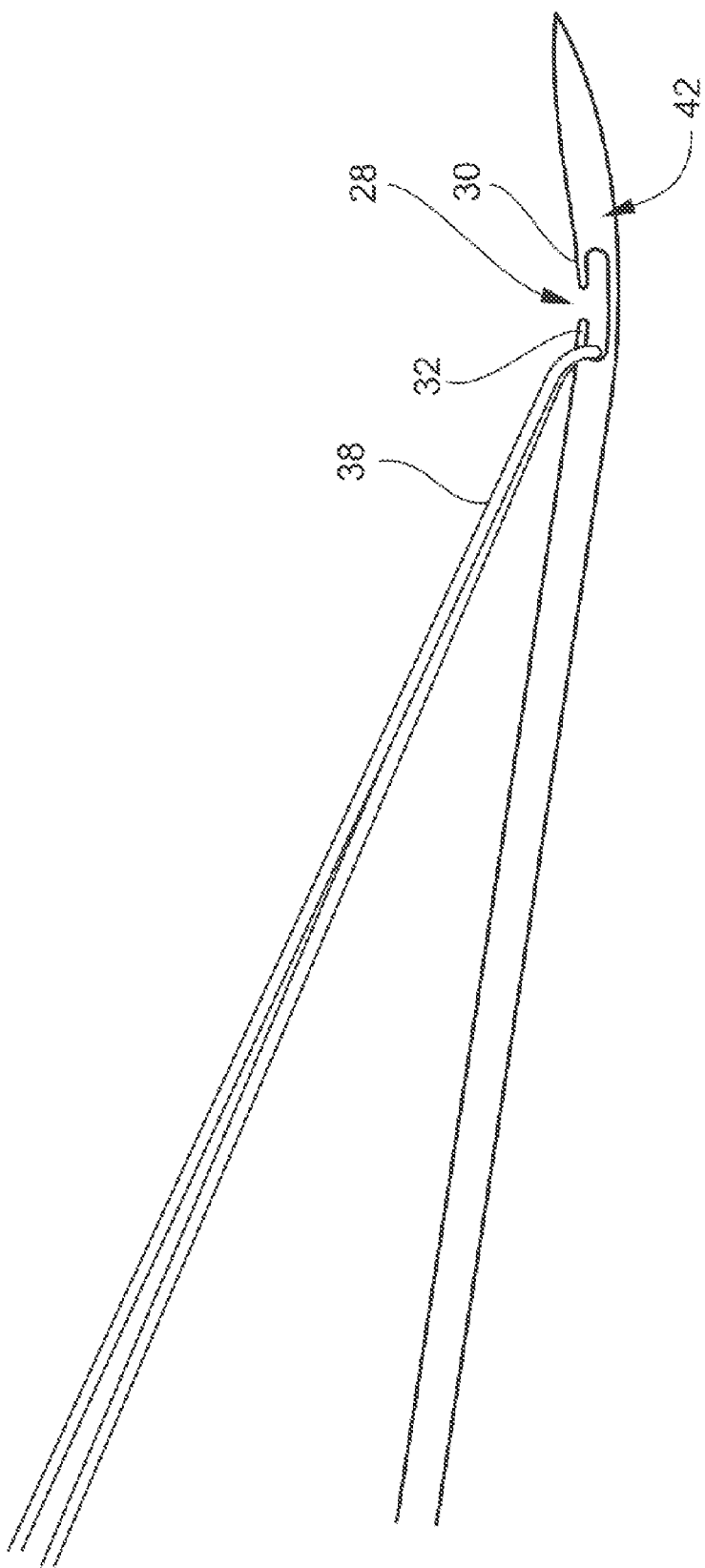
FIG. 3 is an illustration of the suture passer device of the present invention loaded with a suture.

FIG. 3 illustrates a suture passer device of the present invention 10 loaded with a barbed suture. As can be seen in FIG. 3, the suture 38 has been looped around and over proximal hook 32 within mouth 28 and open area 34 of instrument 14 for insertion with the passer 10. The suture 38 has been tightened as indicated by the suture 38 extending in taught manner above instrument 14 and toward a medical professional or fixed point (not shown). In use, the suture passer 10 is inserted into a patient at a desired location and the suture 38 follows the insertion path created by the device 10 as the suture 38 is fixed over hook 32.

Figure 4:
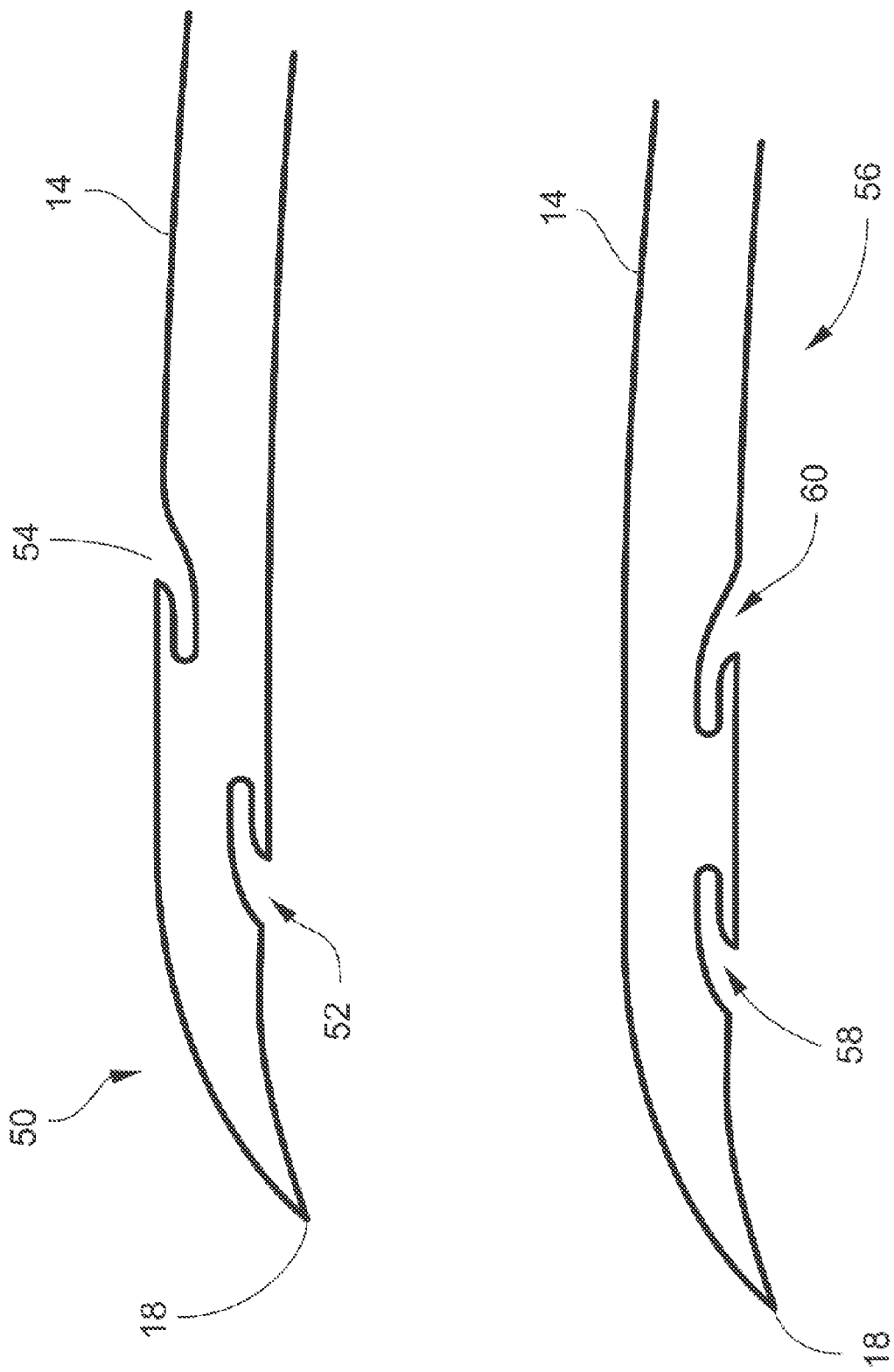
FIG. 4 illustrates alternative positions for the insertion and extraction hooks on the device of the present invention.

FIG. 4 illustrates alternative embodiments of the present invention which include alternate positions for the hooks along the instrument body 14 to receive a suture 38 on the suture passer 10. The insertion hook may be located at any position along the surface of the instrument 14, including closer to the tip 18 of the instrument than an extraction hook. In like manner, the extraction hook may be positioned anywhere along the surface of the instrument 14. This is shown in FIG. 4, first with reference to alternative embodiment 50, which includes the insertion hook 52 located closer to tip 18 of instrument 14 than extraction hook 54. Further, the extraction hook 54 may be positioned on opposite side of instrument 14 from the insertion hook 52. Those of skill in the art recognize that position of insertion hook 52 and extraction hook 54 may be switched in positions and such an embodiment is within the scope of the invention. In alternative embodiment 56, the insertion hook 58 and extraction hook 60 are located on the same side of the instrument 14. The insertion hook 58 is located closer to tip 18 than extraction hook 60 here as well. In these embodiments, the suture 38 may be placed onto the suture passer 10 in similar manner as described herein.

Figure 5A:
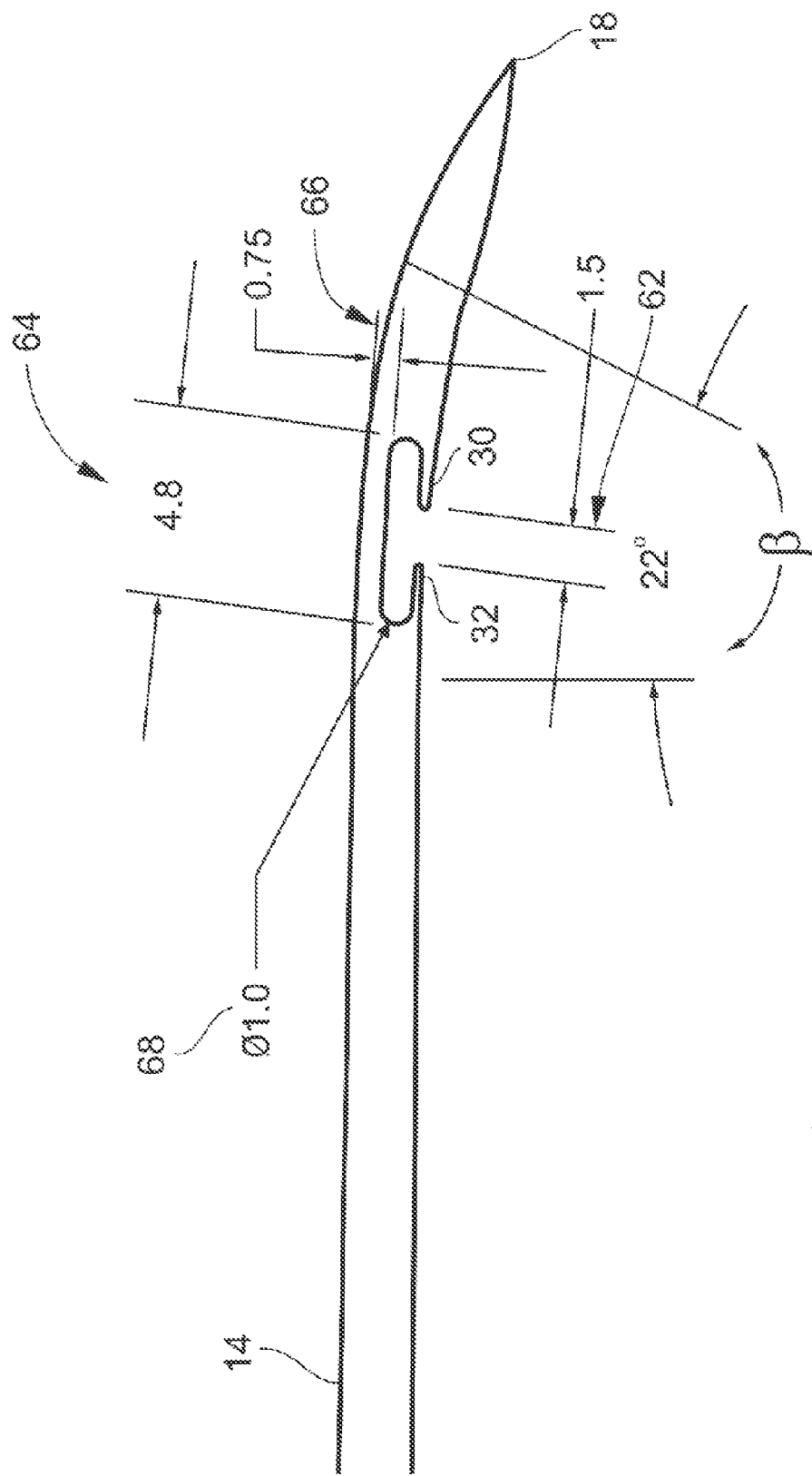
FIG. 5A is schematic diagram of the suture passer of the present invention with relative positioning of features.

FIG. 5A is a schematic to illustrate various non-limiting dimensions of an example of the present invention. In FIG. 5A, there is shown an instrument 14 of the suture passer 10 formed with known suitable materials for suture passers, such as metals, alloys, polymers, composites, etc., and by methods known in the art. The mouth opening 28 of the instrument 14 has a length 62 and is 1.5 millimeters in this example, although a range of approximately 0.5 to 4 millimeters is within the scope. The internal opening 34 formed by the extraction hook 30, insertion hook 32, and the internal surface 36 has a length 64 and is shown as 4.8 millimeters in FIG. 5A. The internal opening 34 and internal surface 36 provide a remaining thickness 66 of approximately 0.75 millimeters to external surface of the instrument 14 from internal surface 36. The diameter 68 is indicated as 1.0. An angle from the body 23 of instrument 14 to head 26 of instrument is also shown, and in this particular example, the angle is 22 degrees.

Figure 5B:
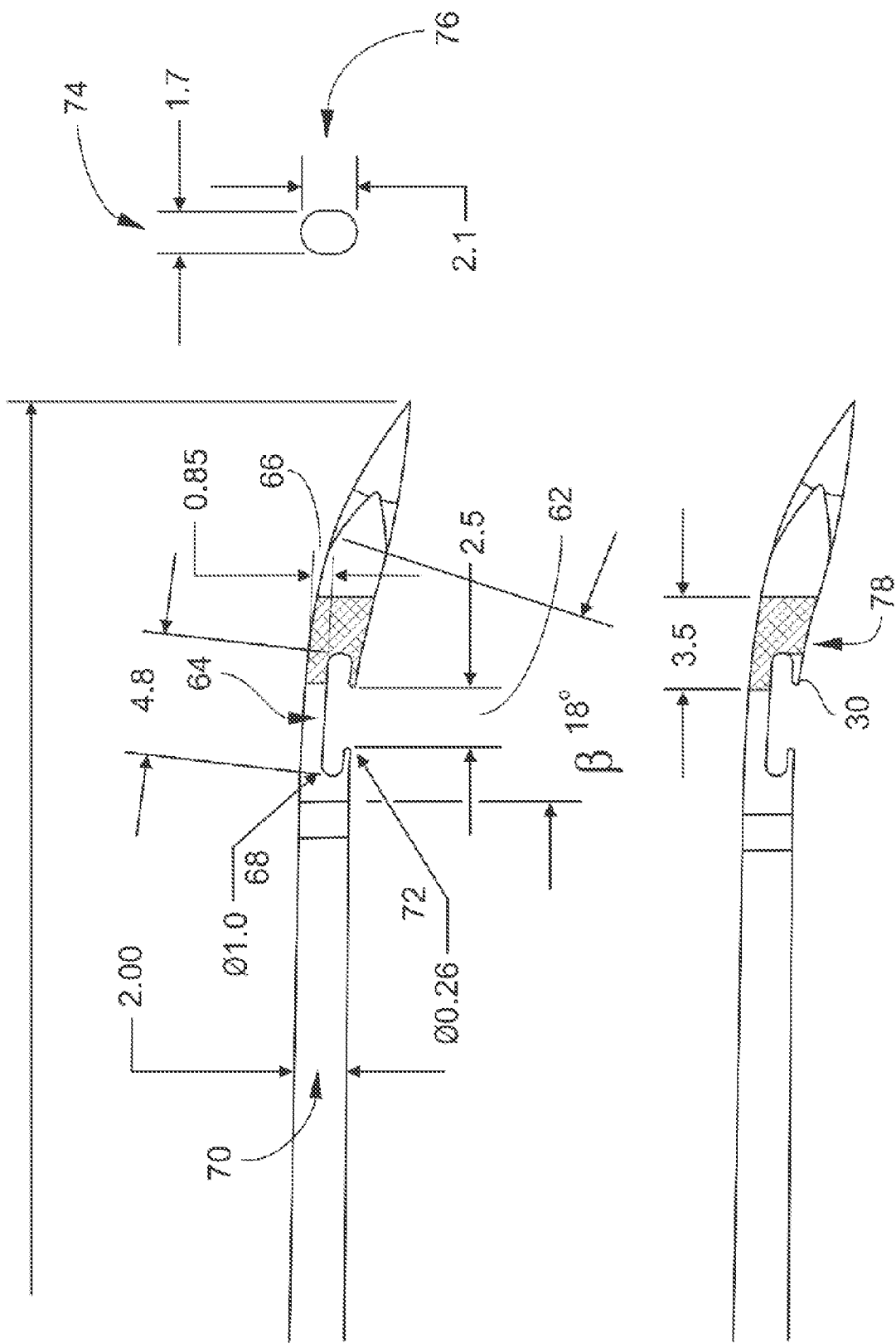
FIG. 5B is schematic diagram of the suture passer of the present invention with relative positioning of features.

A second non-limiting example is shown in FIG. 5B, where there is again shown an instrument 14 of the suture passer 10 formed with known suitable materials for suture passers, such as metals, alloys, polymers, composites, etc., and by methods known in the art. The mouth opening 28 of the instrument 14 has a length 62 and is 2.5 millimeters in this example. The internal opening 34 formed by the extraction hook 30, insertion hook 32, and the internal surface 36 has a length 64 and is shown as 4.8 millimeters in FIG. 5B. The internal opening 34 and internal surface 36 provide a remaining thickness 66 of approximately 0.85 millimeters to external surface of the instrument 14 from internal surface 36. The diameter 68 is indicated as 1.0. An angle from the body 23 of instrument 14 to head 26 of instrument is also shown, and in this particular example, the angle is 18 degrees. A body thickness 70 is shown as 2.0 millimeters. The insertion hook 32 in FIG. 5B has a diameter 72 of 0.26 millimeters. The instrument in this example has an oval shape and there is also provided a width 74 of 1.7 millimeters and height 76 of 2.1 millimeters. A visually marked area 78 near extraction hook 30 is shown as 3.5 millimeters in this non-limiting example.

Figure 6:
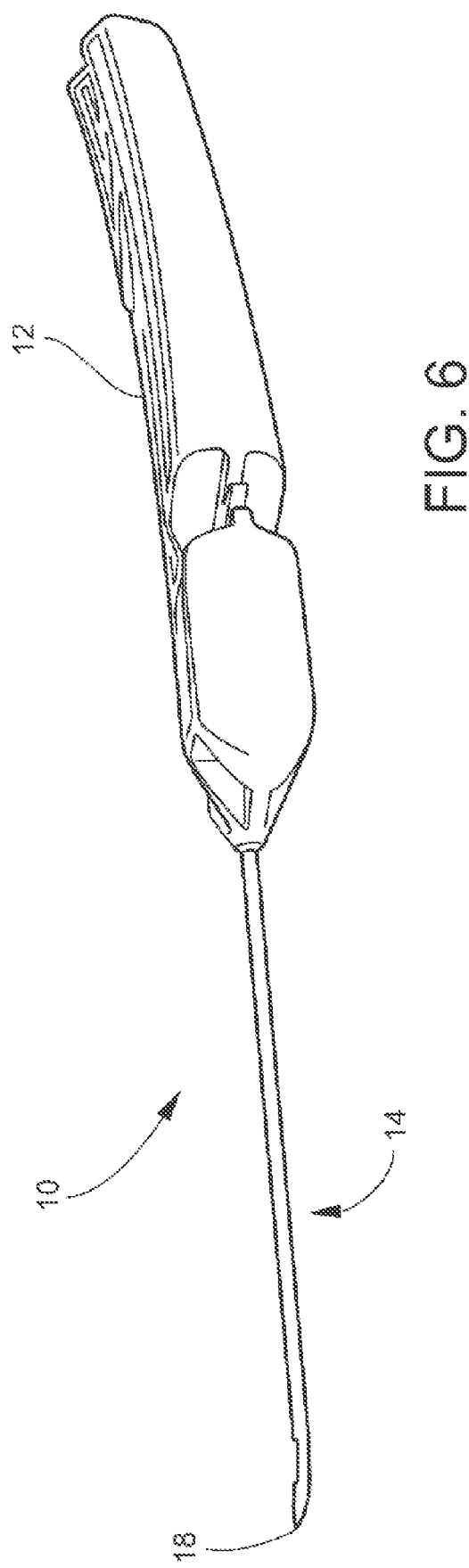
FIG. 6 is another view of the suture passer device of the present invention.

FIG. 6 is another view of the suture passer device 10 of the present invention. The handle grip 12 may be made of materials and methods known in the art and may include grooves, ridges, or other means for aiding a medical professional to hold the device 10. The handle 12 length similarly may be of any sufficient size to allow the medical profession to grasp the overall device 10 and have ease of maneuverability with the device during procedures. The handle includes an opening or similar means at an end for receiving the instrument 14 and is fastened by fastening means and methods known in the art. An internal stabilizing piece 22 is also used for receiving end of the instrument 14 as well as support. In an embodiment, the handle 12 is an integrated part of the instrument 14, and without the need for separate fasteners or separate instrument and handle sections.

The overall length of the instrument 14 from the handle 12 to the tip 18 may be a range of approximately 6 centimeters to 12 centimeters, with 9 centimeters as fitting for surgical procedures within the scope herein. The instrument 14 is of sufficient length to enter a patient's neck and penetrate tissue past the hyoid bone and tongue base and into the patient's throat cavity and airway area during a surgical procedure. In this manner the suture passer with a loaded suture can be visible to a camera attached to a robotic arm and flex system which is inserted into a patient's mouth during surgery. The images from the camera are sent to a display for the medical professional's live viewing during surgery.

Figure 7:
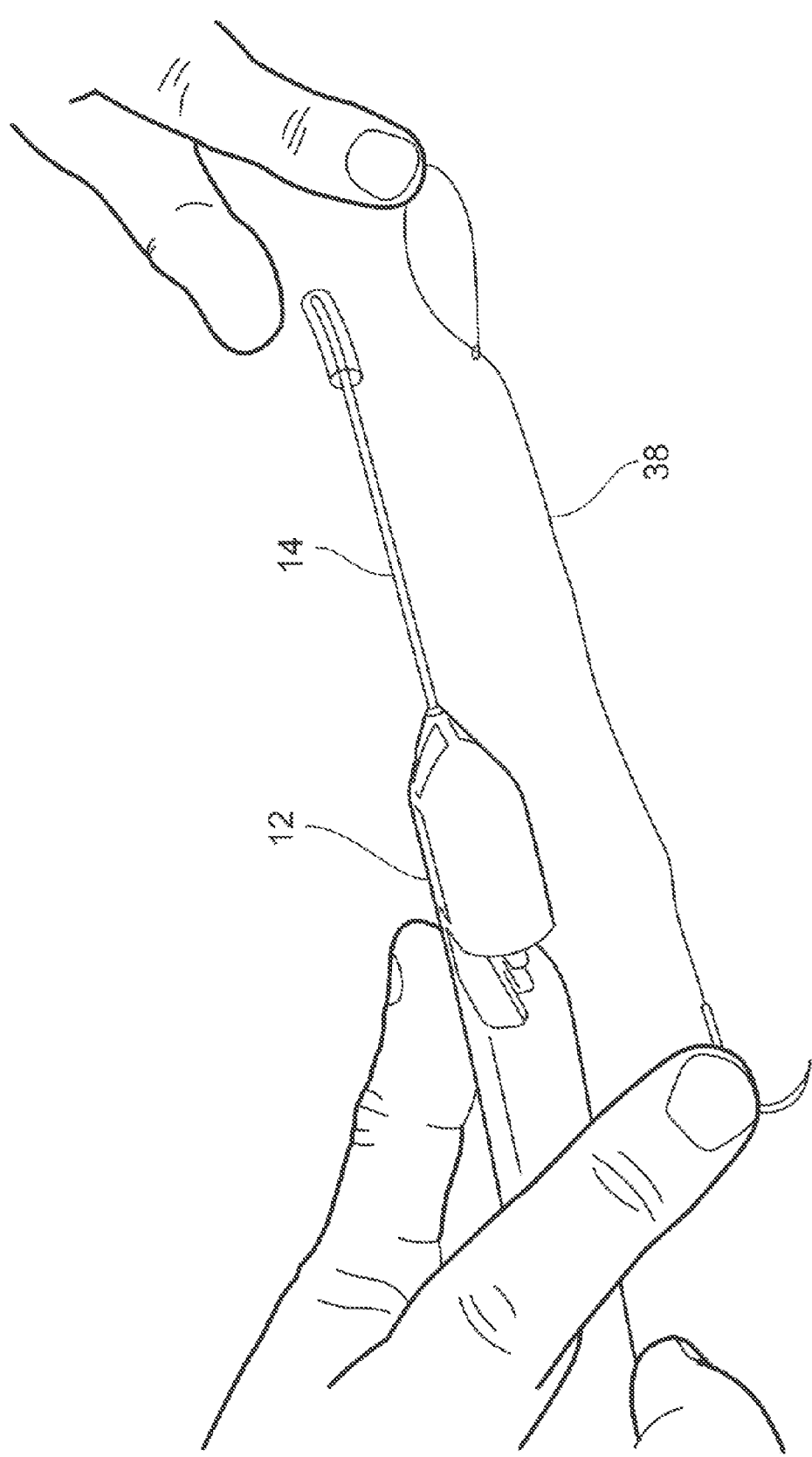
FIG. 7 is the suture passer of the present invention placed next to a barbed suture.

FIG. 7 illustrates the suture passer 10 of the present invention adjacent to a barbed suture A No. 2 barbed suture is suitable for the device of the present invention, although other sutures known in the art are suitable for use with the suture passer device 10. The suture 38 is of sufficient length to extend with the suture passer into a desired surgical area Referring to FIG. 8 there is shown the suture passer device of the present invention 10 in use with patient 202 receiving the medical procedure 200. The suture passer 10 is shown held by a medical professional 216 at its handle 12 as the needle tip 18 of the device 10 is inserted at the midline 206 of the neck 204 of the patient 202. The patient 202 during this procedure of robotic surgery has robot arm 208 inserted through his mouth while clamp 214 holds the patient's mouth in open position and a tongue blade 212 is used to position the tongue for the surgery. The suture passer 10 enters the neck 204 at the midline 206 just under the location of the hyoid to deliver a barbed suture attached to the suture passer at the insertion hook.

Figure 9:
FIG. 9 is a surgical procedure with the present invention viewed on a monitor.

Referring now to FIG. 9 there is illustrated a television monitor 220 which provides the image from inside the patient from cameras attached to the robot 208 which have been inserted into the patient's mouth and throat. A medical professional 216 can view the images of the suture passer device 10 entering the tongue base/vallecula. The suture passer 10 is loaded with barbed suture 38 and brought to a position far enough away from the tongue base so that medical professional 216 may begin work with the robotic instrument and have visibility in the surgical area inside the mouth of the patient 222. This is the insertion step of the process with the suture passer in a first position.

Figure 10:
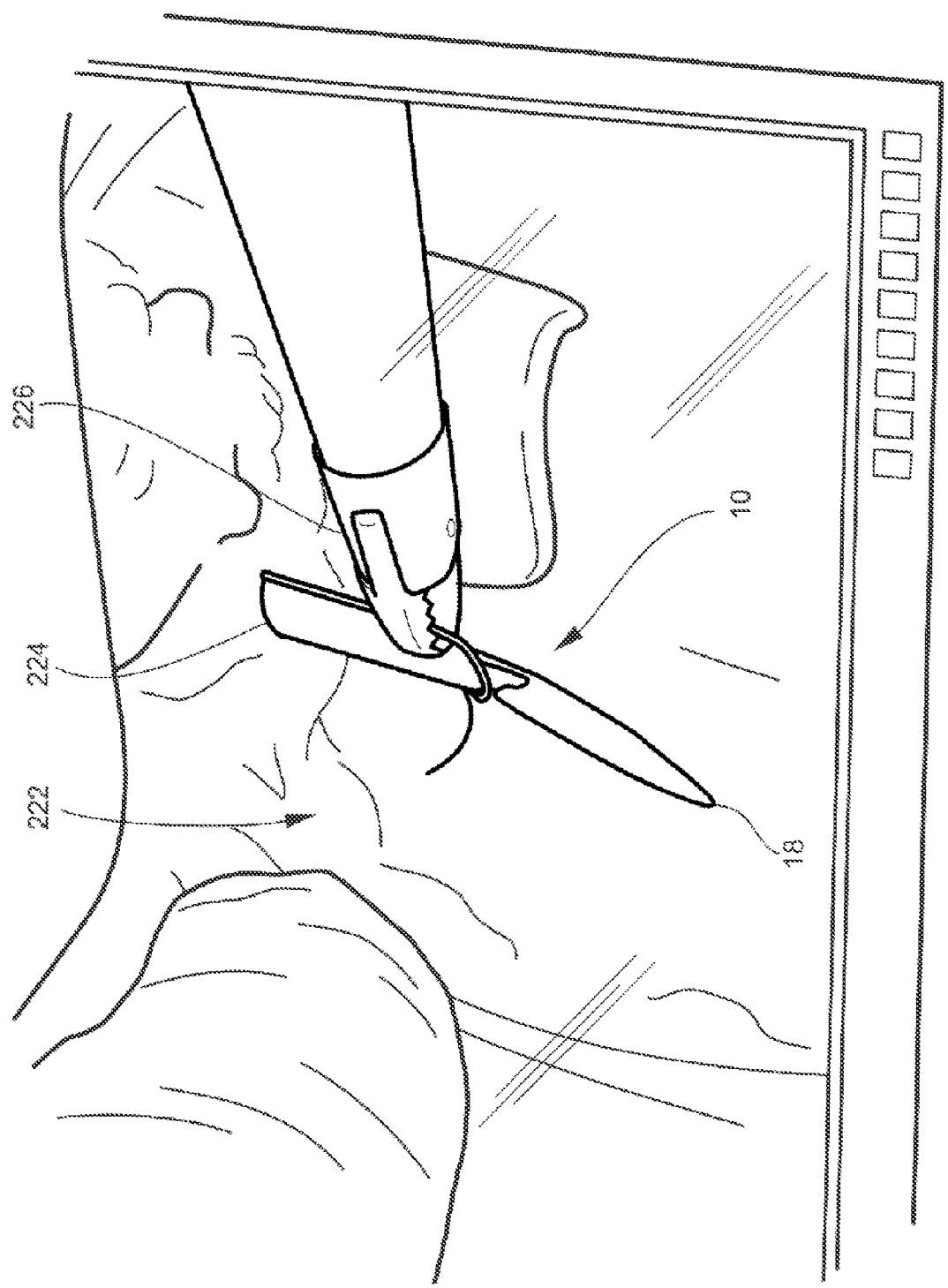
FIG. 10 is robotic forceps grasping and releasing the suture from the suture device during a surgical procedure.

As seen in FIG. 10 the inside of the mouth and surgical area of patient 222, there is shown forceps grasping and releasing the barbed suture 38 which has been fastened to the suture passer 10. The suture passer 10 is shown protruding from the first opening 224 created when tip 18 of the suture passer 10 pierced the tissue. The suture passer 10 and its elongated body 14 extend through the tissue with suture 38 fastened to insertion hook 32. During this time the tongue blade remains in position as it exposes the center compartment of the tongue base.

Figure 11:
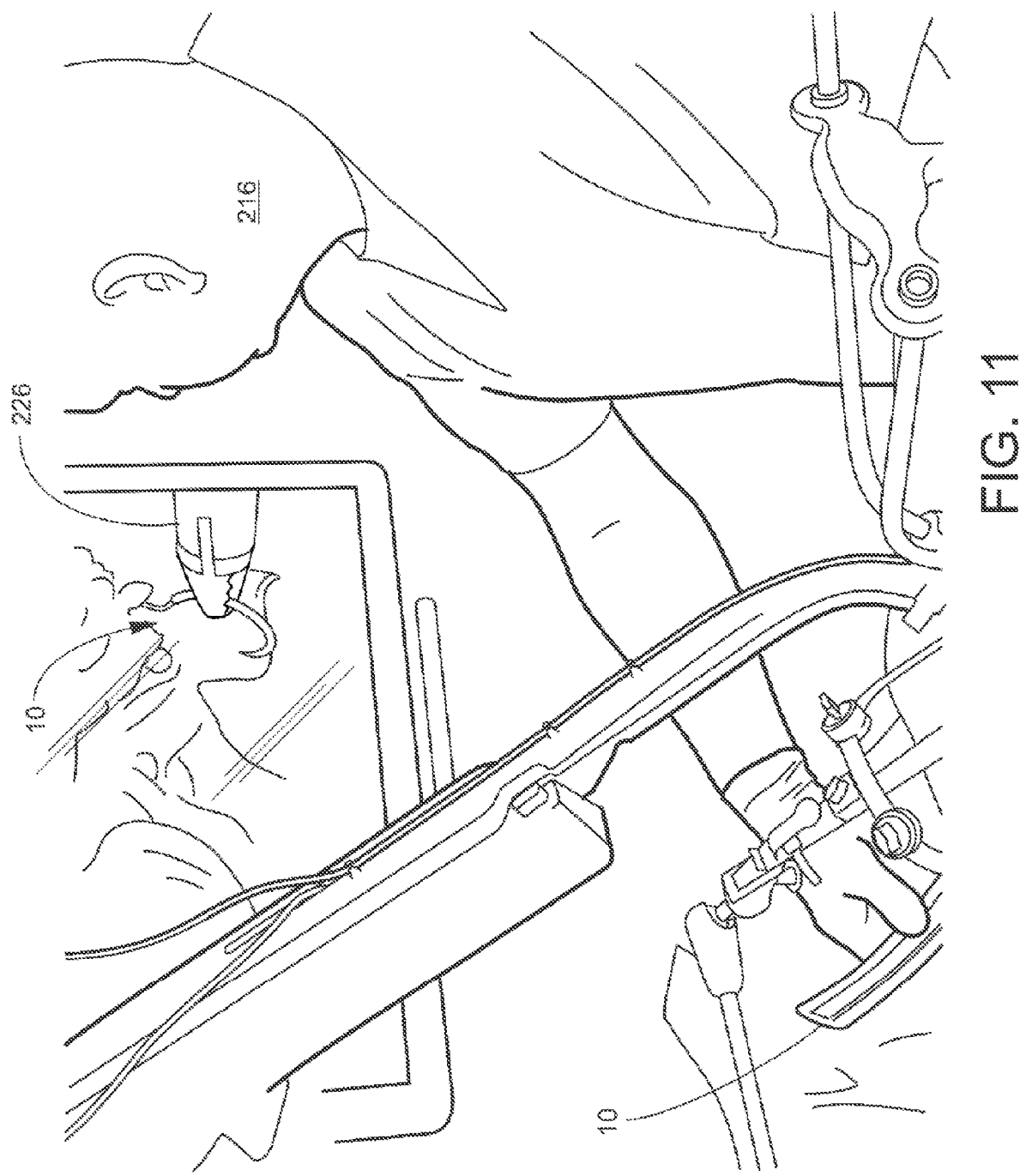
FIG. 11 is an illustration of the robotic forceps reloading the suture onto the suture passer extractor of the present invention.

Referring now to FIG. 11 there is shown again the medical professional 216 viewing the monitor 220 and using the forceps 226 to reload the barbed suture 38 onto the suture passer 10 at the extractor hook 30.

Figure 12:
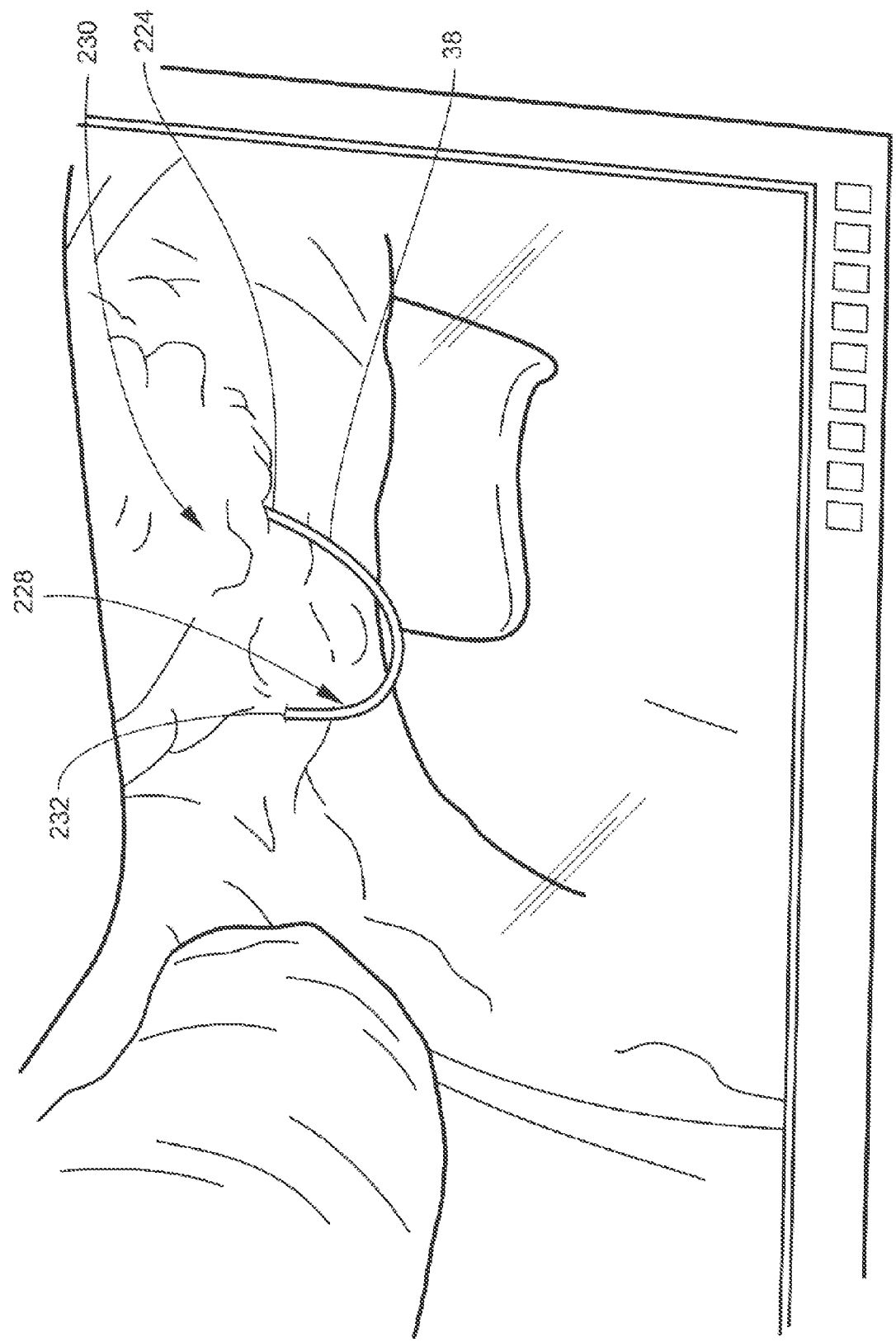
FIG. 12 is a schematic of a suture loop along the tongue base and around the hyoid after use of suture passer of the present invention with robotic assisted surgery.

In FIG. 12, the device of the present invention 10 has been extracted through a second position. As can be seen, the suture 38 forms a suture loop 228 from entering insertion opening 224 and returning through extraction opening 232. The suture loop 228 loops along the tongue base and around the hyoid before suspension is performed.

Figure 13B:
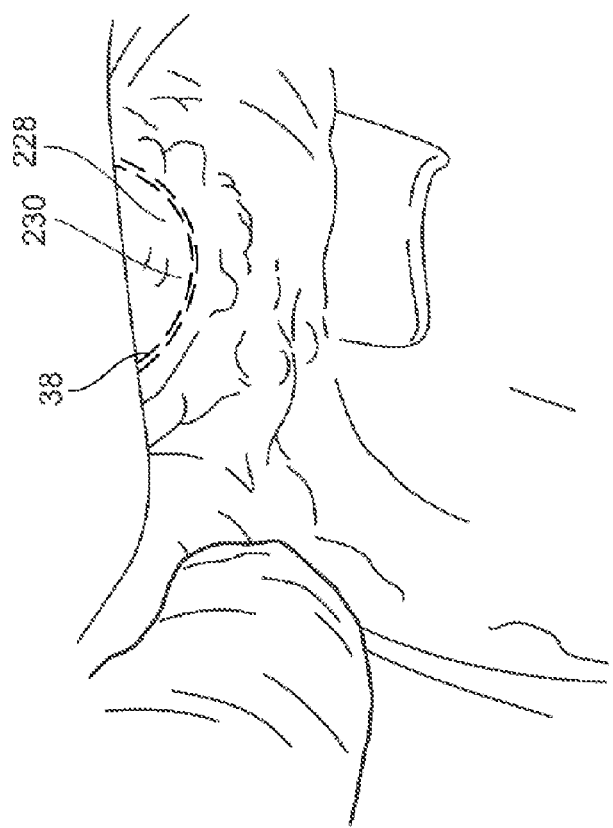
FIGS. 13A and 13B illustrate a suture loop along the tongue base and around the hyoid, initiating the suspension process.
Figure 13A:
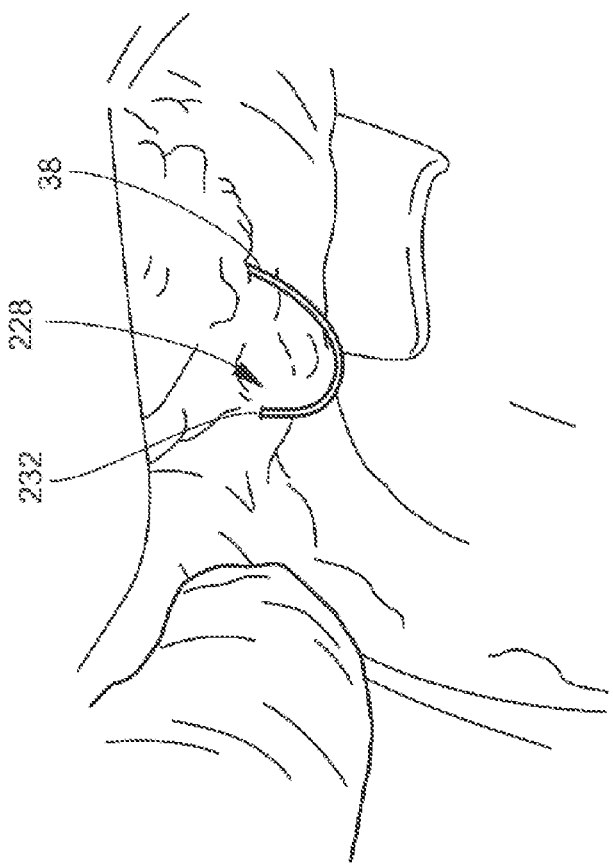

Referring to FIGS. 13A and 13B there is shown the suture loop 228 along the tongue base and around the hyoid initiating suspension. The suture loop 228 is pulled upward through insertion opening 224 and extraction opening 232. As shown in FIG. 13B the suture loop 228 pulls the tissue upward enlarging the cavity opening inside the patient. This will assist in providing a clear respiratory path for a patient who suffers sleep apnea.

Figure 14A:
FIG. 14A illustrate a suture loop along the tongue base and around the hyoid, indicating partial suspension.
Figure 14B:
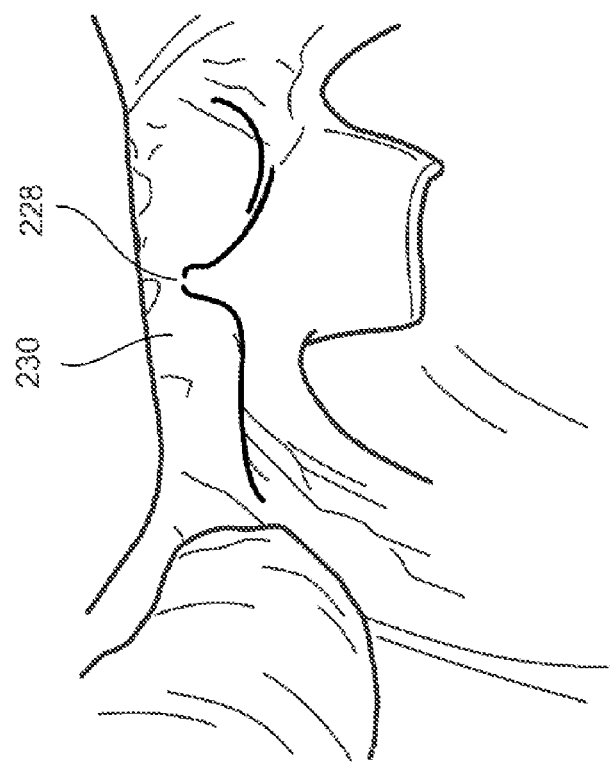
FIG. 14B illustrate a suture loop along the tongue base and around the hyoid, indicating complete suspension.

Referring to FIGS. 14A and 14B there is shown the suture loop 228 along the tongue base and around the hyoid 250. In FIG. 14A there is shown partial suspension of the tissue. In FIG. 14B there is shown complete suspension.

Figure 8:
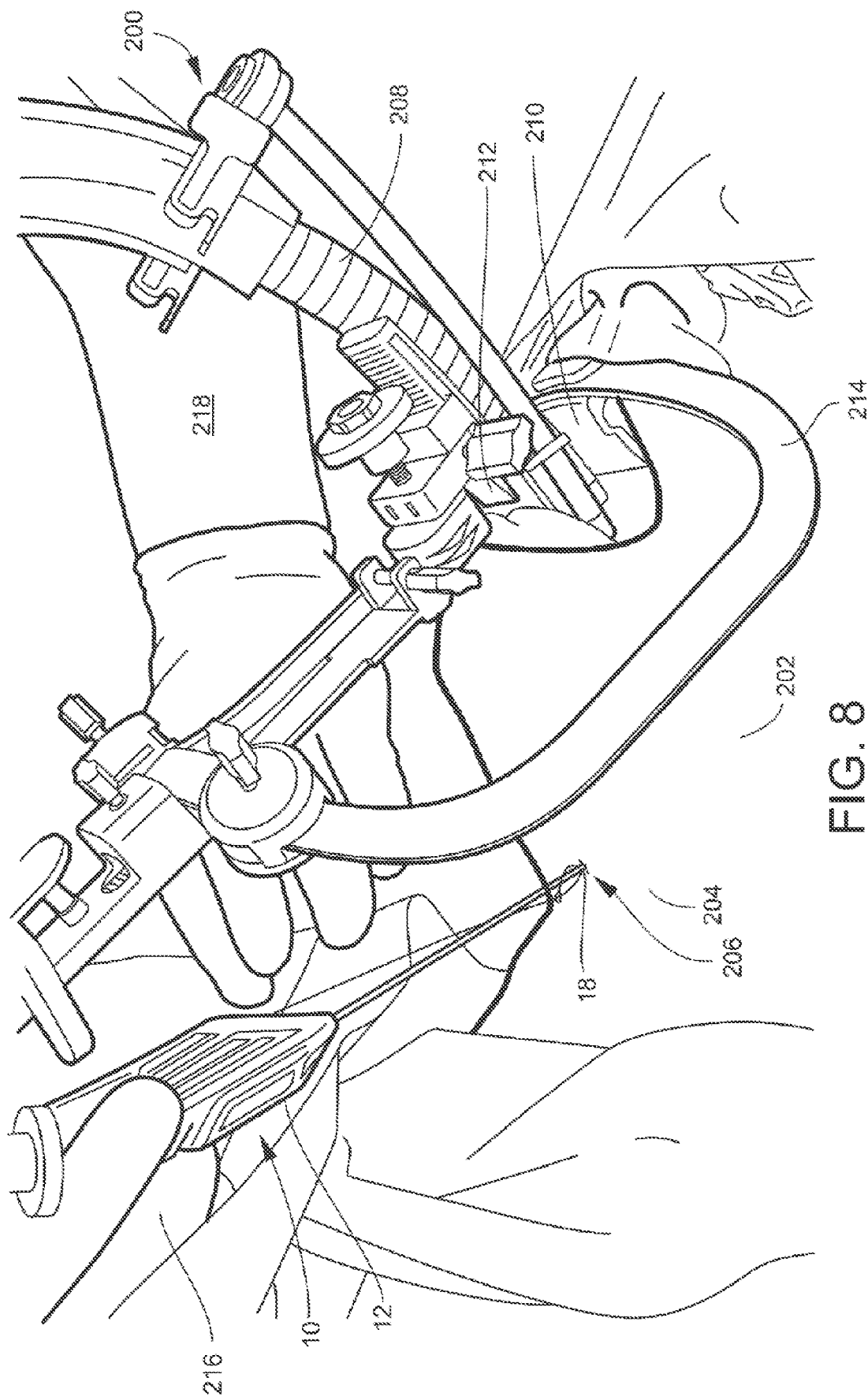
FIG. 8 is the suture passer of the present invention in use on a patient during a medical procedure with robot assisted minimally invasive surgery.

Referring to FIG. 15 there is shown a cross-section of a patient 240. This patient 240 is undergoing a robotic surgery with the device of the present invention 10. Nasal tracheal intubation 262 is inserted through nostril 260 of patient's nose 258. The robot arm 252 has been inserted through the patient's mouth 256 with the robotic flex system 254 extending into the patient's throat. The robotic flex system includes a camera with light 255 for visibility in the area of the medical procedure. Forceps may be attached with the flex system as well. Within FIG. 15 there is shown hyoid bone 250, epiglottis 264, and lingual tonsil 266 as part of tongue base. Mouth 256 and mandible 268 are maintained in position during surgery by clamp 214 (FIG. 8). As shown in FIG. 15 the suture passer of the present invention 10 is inserted at a single entry point 244 from a first position 242 so that tip 18 and elongated body 14 of the suture passer 10 pass over the hyoid bone 250. In this manner tip 18 of suture passer having barbed suture 38 loaded onto insertion hook will pass over the hyoid bone and through tongue base into throat cavity of patient 240. The forceps of flex system and robotic arm 252 at this point can grasp the suture 38 from the suture passer 10 and release the suture 38 from the suture passer 10. Since the suture 38 has to make a loop, the entry and exit of the suture 38 (around the hyoid) needs to be in different locations. To achieve this, the suture passer 10 is moved to a second position 270 without removing the suture passer through the entry point 244. The curved tip and angled head section 26 at second end 17 of the instrument 14 (See, FIGS. 1 and 2) facilitates this action as the surgeon can rotate the handle 12 and puncture the tongue tissue in a second location for exit of the suture 38 which is different than the initial entry location of the suture 38. The suture passer 10 in second position 270 will pass below the hyoid bone 250 and tip 18 will extend into patient's throat cavity n the surgical area. The suture 38 which has been held by forceps of flex system 254 will now be loaded onto the extractor hook 30 of the suture passer 10. In this manner the suture 38 has entered at a first position and exits at a second position to loop around the hyoid bone. Those of skill in the art will note that position one 242 of device 10 and position two 270 may be done in either order.

Referring to FIG. 16 there is shown the internal view of FIG. 15. In this Figure, suture passer of device 10 enters through insertion opening 224 with suture 38 loaded onto insertion hook 32 within mouth 28 of the suture passer. The suture passer 10 as can be seen from insertion opening 224 passes over hyoid bone 250 and over lingual tonsil area. The tip 18 extends past epiglottis. In this manner the device of the present invention 10 and elongated body 14 extend through insertion opening 224 with suture 38 to a sufficient distance allowing medical professional increased visibility in surgical area. The suture 38 is unloaded from suture passer 10 by robotic forceps. The suture passer 10 is then moved to a second position 270 behind hyoid bone 250 and behind lingual tonsil 266. The empty suture passer 10 in position two may now receive suture 38 into extraction hook 30. As can be seen in FIG. 16 nasal tracheal intubation 262 remains in place for patient.

FIG. 17 is an illustration of patient 240 receiving nasal tracheal intubation 262 and in preparation for robotic surgical procedures in use of the device of present invention 10. Patient 240 has safe zone 272 located along the anatomical midline landmarks for the chin 274 and sternal notch 276. The safe zone 272 is located in patient's throat below chin and is the location for the suture passer device of the present invention to enter the patient's body.

Figure 18:
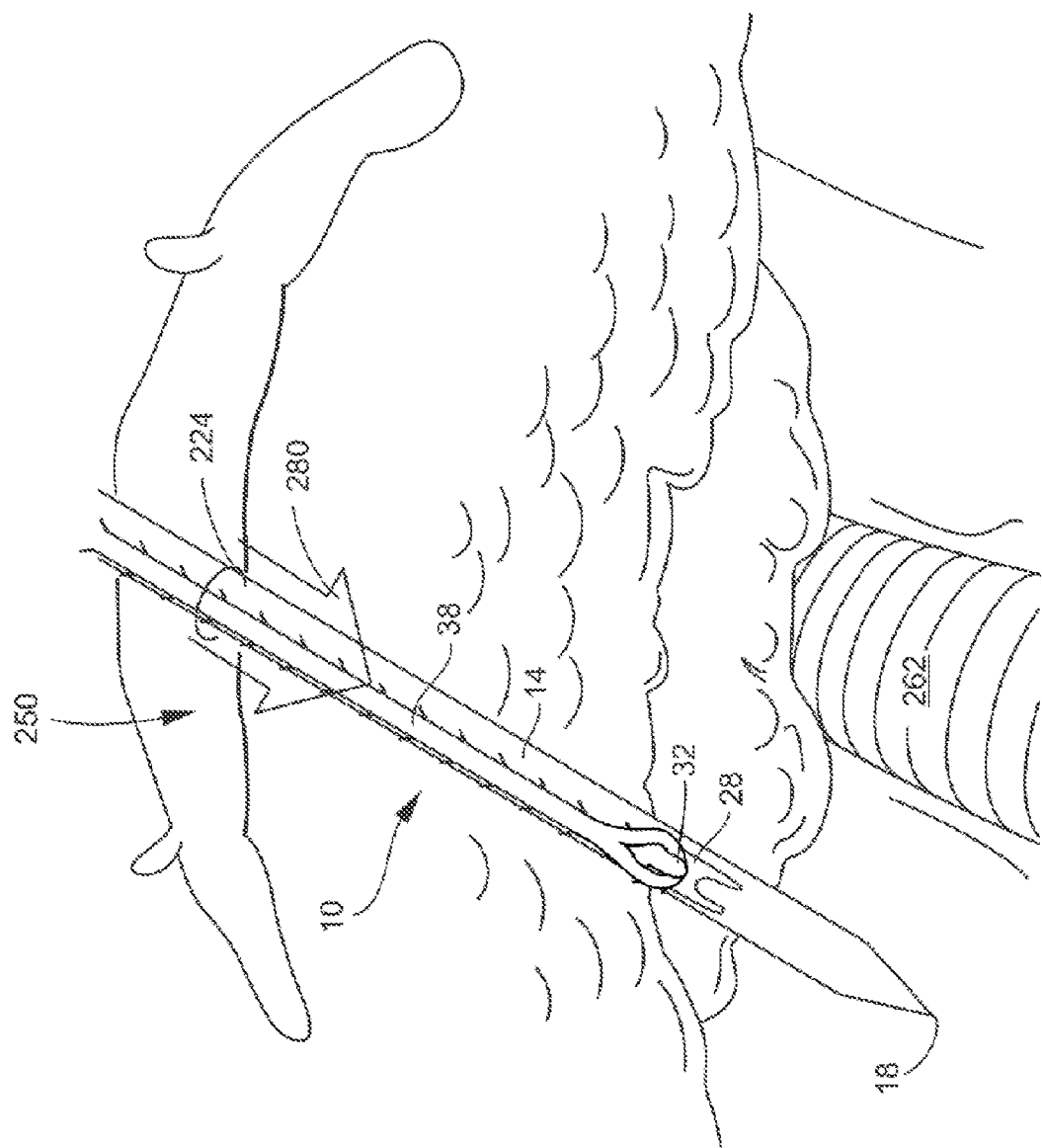
FIG. 18 is the suture passer of the present invention loaded with a suture and inserted above the hyoid.

As the suture passer 10 is inserted into safe zone 272 it will be inserted above the hyoid bone 250. This is shown in FIG. 18 where the suture passer 10 acting as inserter and loaded with barbed suture 38 penetrates tissue creating insertion opening 224 as the suture passer 10 is pressed downward as indicated by insertion movement demonstrated by insertion arrow 280. The suture 38 has been loaded around and under insertion hook 32 previously by the medical professional so that suture 38 received in mouth 28 and under hook 32, so that the suture 38 may pass down into the patient and over the hyoid bone 250 and extend with the suture passer into the throat cavity of the patient. Intubation tube 262 is also shown in FIG. 18 indicating the close proximity of the surgical area.

Figure 19:
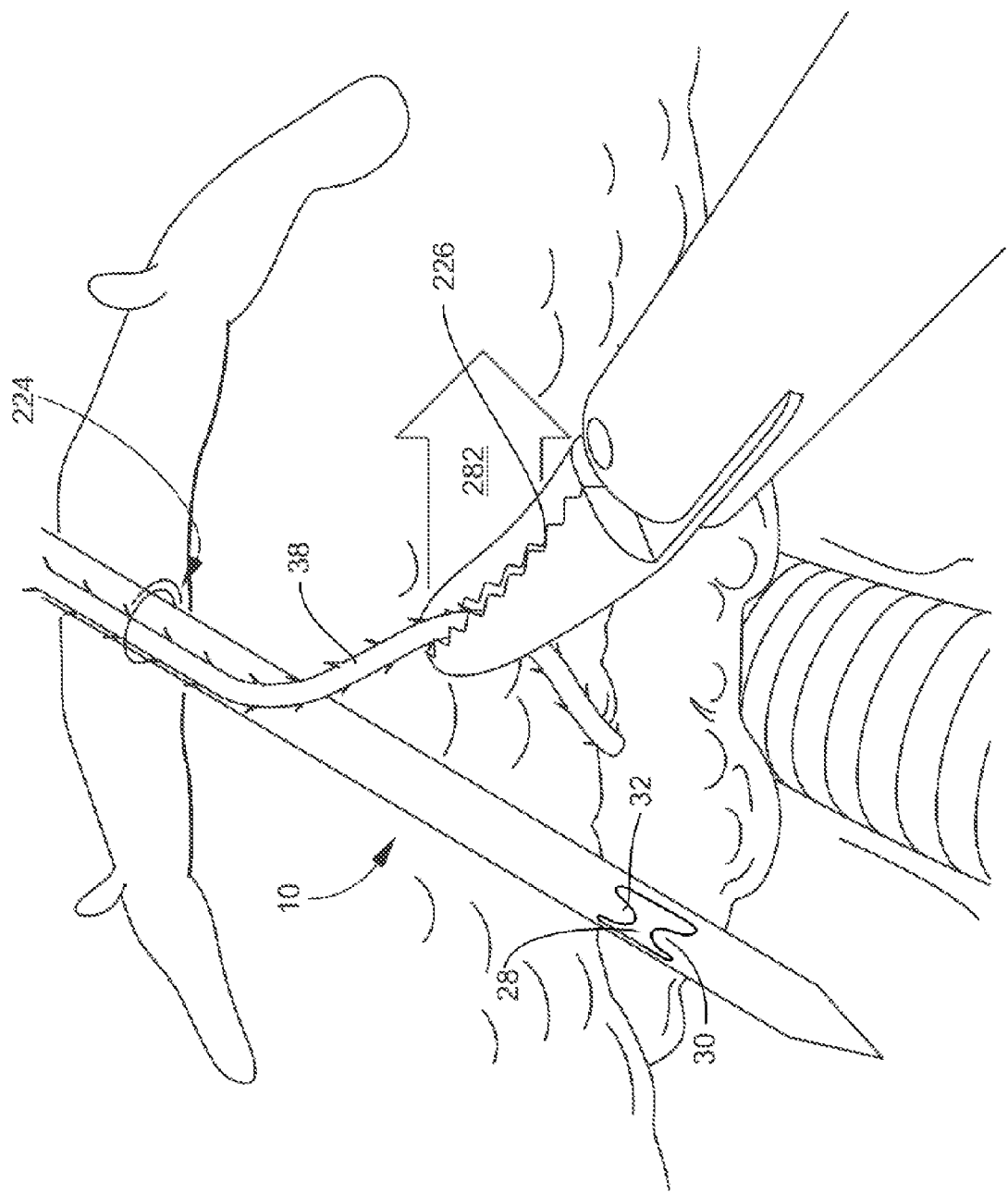
FIG. 19 illustrates robotic forceps grasping a suture from the suture passer device of the present invention.

In FIG. 19, the robotic arm with robotic forceps 226 is shown with the suture passer device 10 in the surgical area from FIG. 18. The robotic forceps 226 grasps and releases the barbed suture 38 from the suture passer 10 and the insertion hook 32 over the mouth 28 along the body of the instrument 14. The robotic forceps 226 moves the suture 38 away from the suture passer 10 as indicated by arrow 282.

Figure 20:
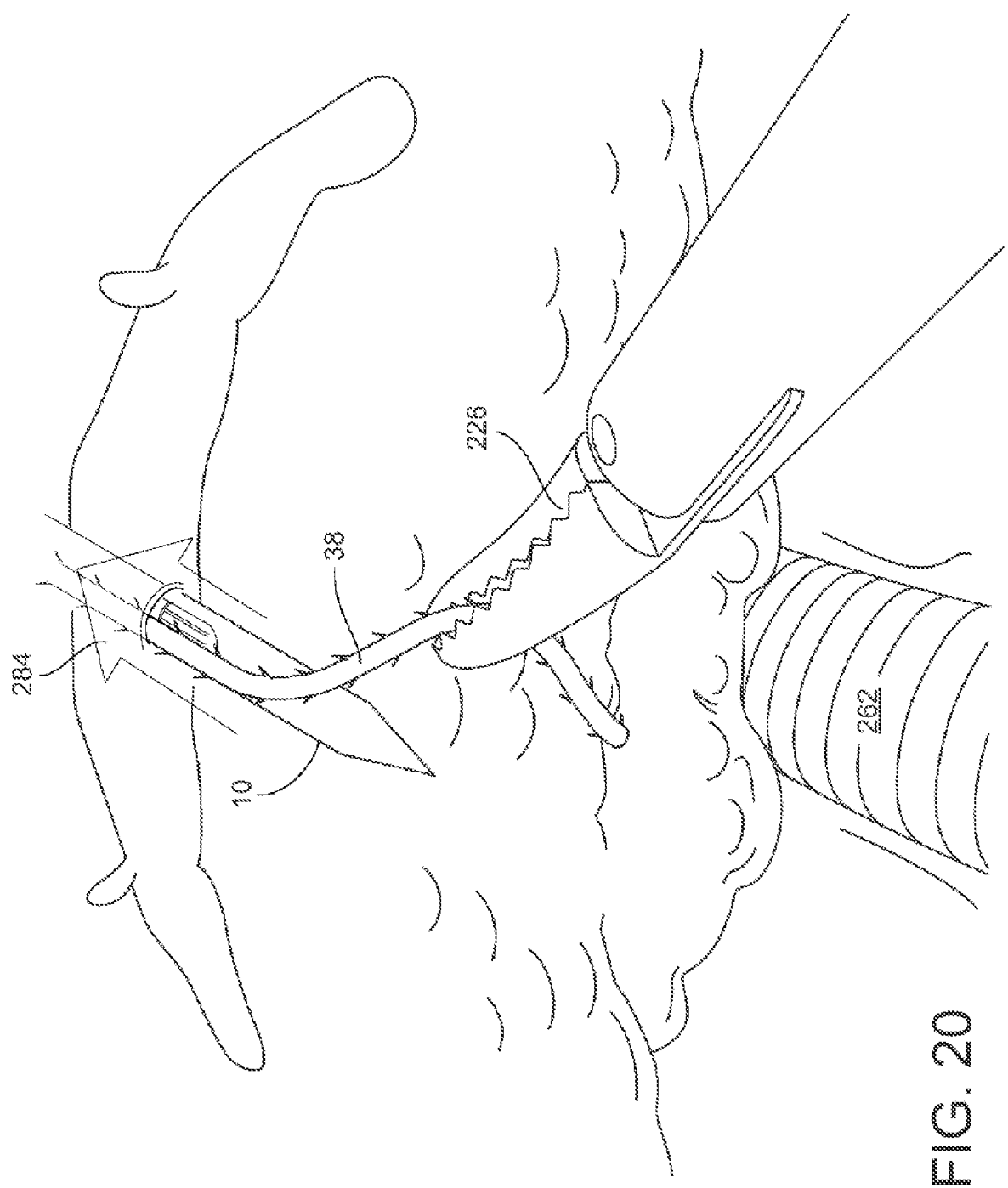
FIG. 20 is an illustration of the suture passer withdrawn empty as the forceps holds the suture.
Figure 21:
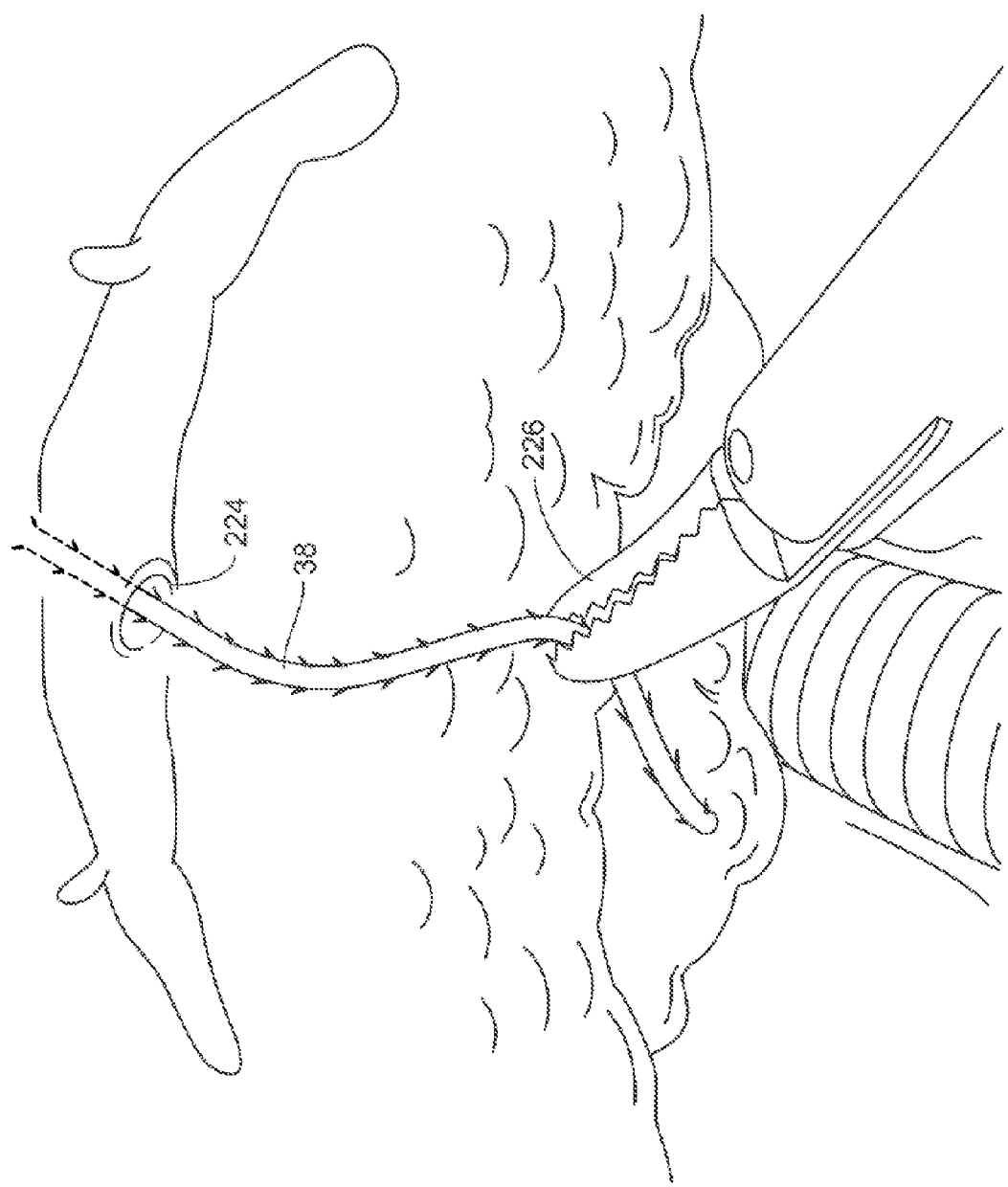
FIG. 21 is an illustration of the suture passer extracted as the suture is held by forceps.

Continuing the procedure in FIG. 20, as the forceps 226 holds the suture 38 the suture passer 10 of the present invention is withdrawn empty back through insertion opening 224. This is indicated by direction arrow 284 in FIG. 20. With FIG. 21, the suture passer 10 of the present device has been fully extracted and the forceps 226 remains holding the suture 38.

Figure 22:
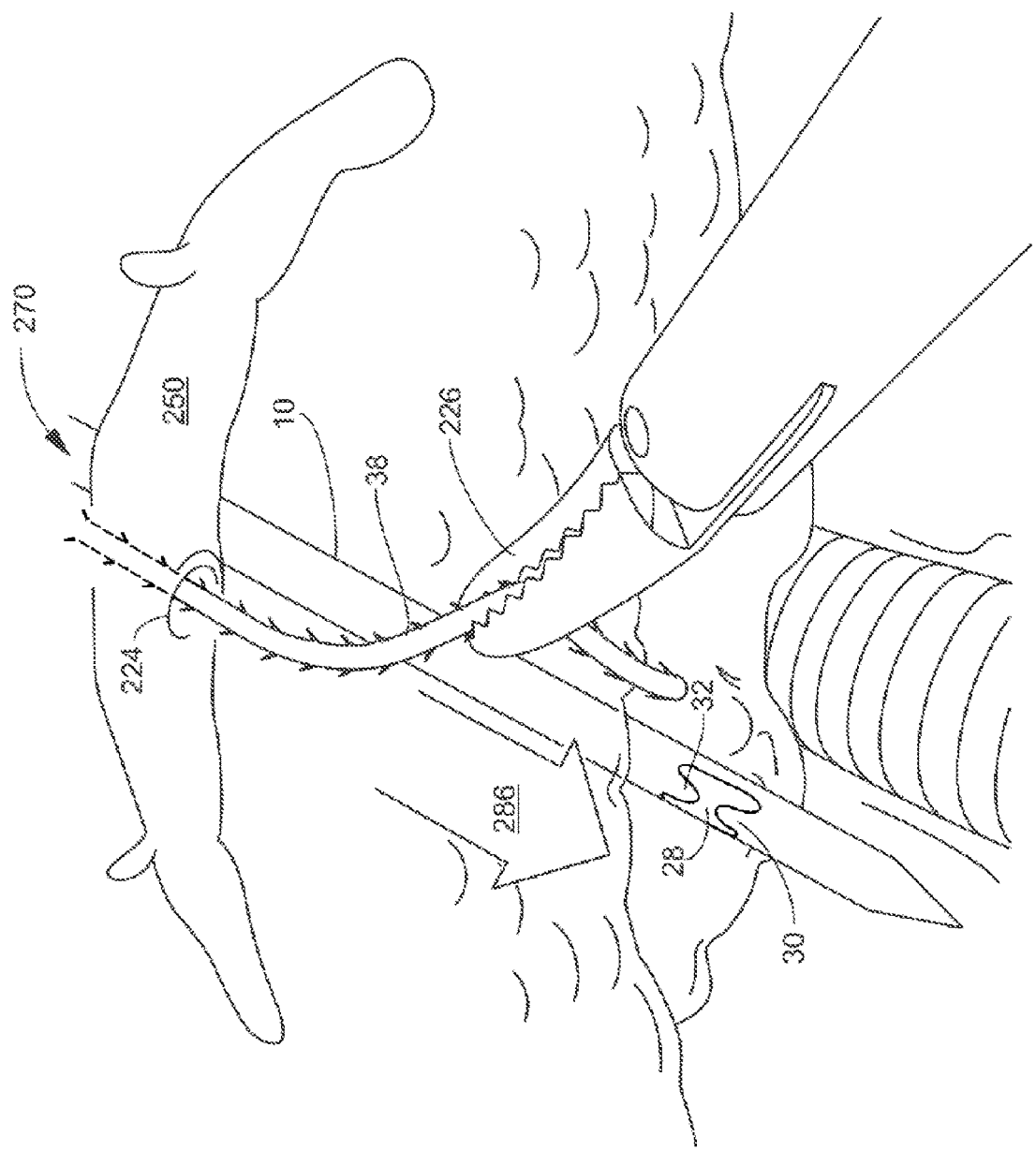
FIG. 22 is an illustration of the empty suture passer entering the tongue base below the hyoid.
Figure 23:
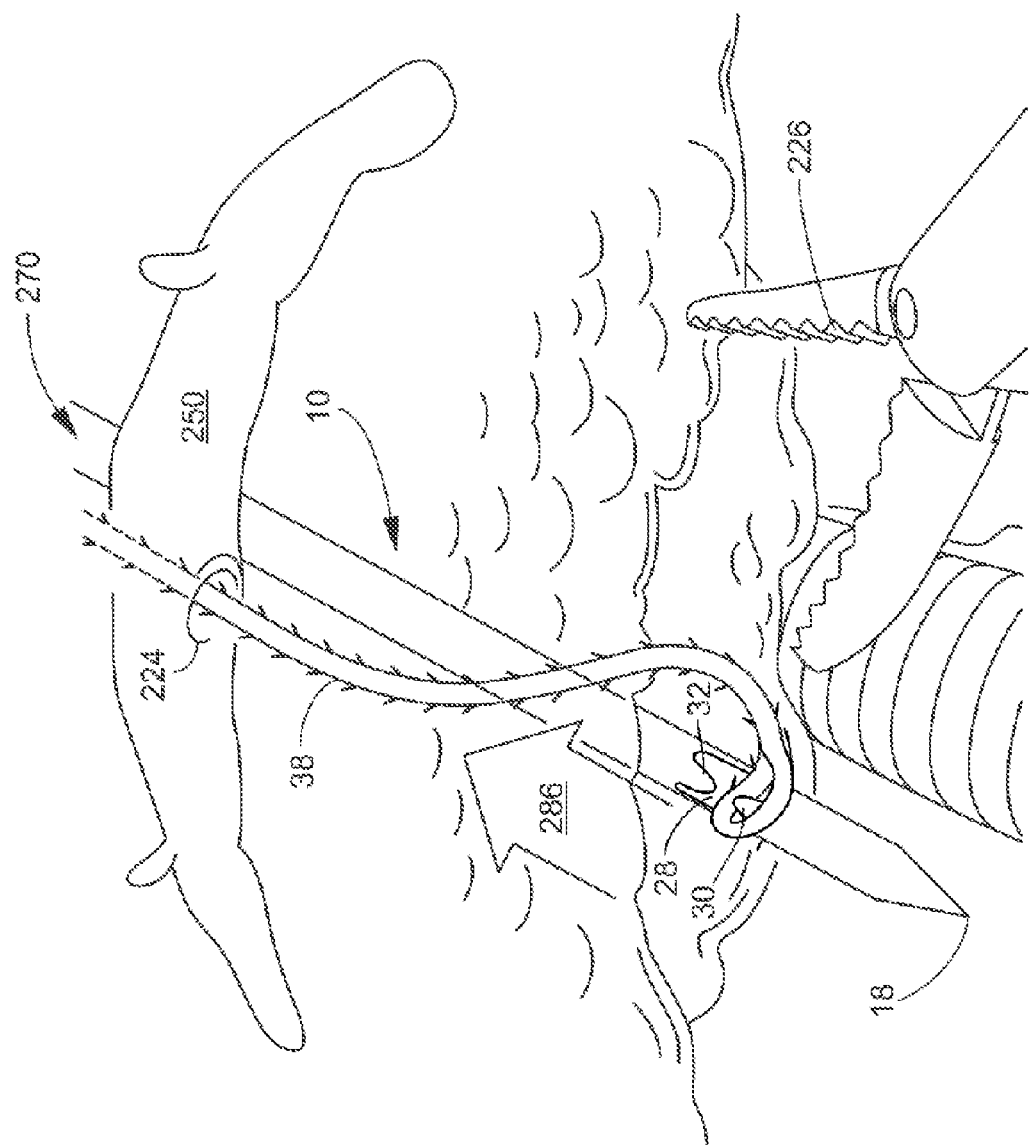
FIG. 23 is an illustration of the suture passer of the present invention reloaded with a suture in the extractor position.

In FIG. 22, the suture passer (empty) enters the tongue base below the hyoid 250 in a second position 270. The forceps 226 is shown still grasping the suture 38, which is extending from insertion opening 224. As the suture passer 10 moves downward as indicated by direction arrow 286, the mouth 28 and hooks 30 and 32 on the instrument 14 become visible to the surgeon by the robotic camera.

The medical professional reloads the suture 38 with the forceps into the mouth 28 located on suture passer 10. This time, the suture is loaded onto extraction hook 30 which is located closer to the tip 18 in this embodiment. Once the barbed suture 38 has been reloaded onto the suture passer in the extraction position, the suture passer 10 may begin withdrawing and extracting from the surgical area and patient. This is indicated by withdrawal arrow 286. The forceps 226 are shown in open position after the suture 38 has been fastened to the suture passer.

Figure 24:
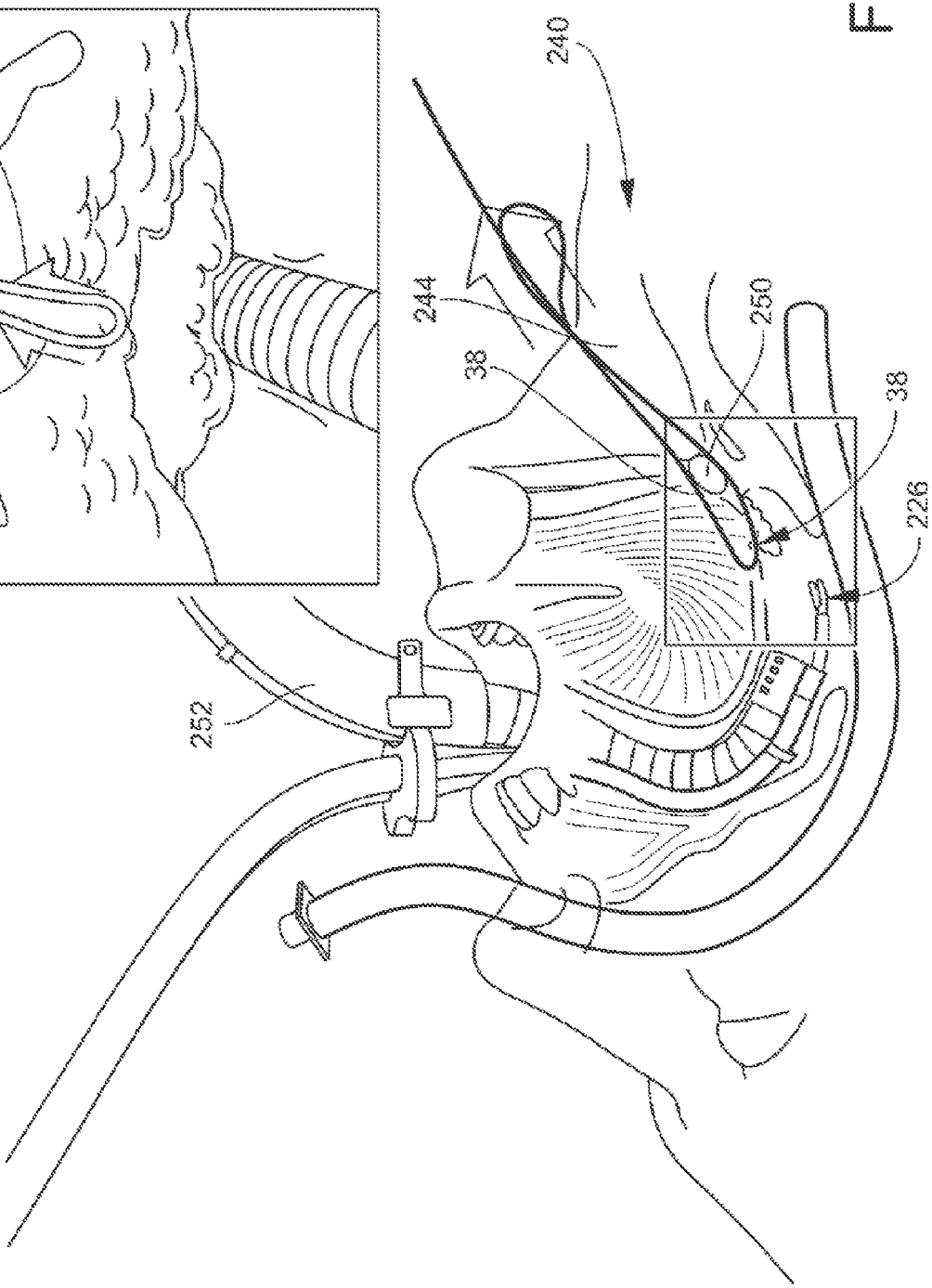
FIG. 24 is cross section of a patient with the suture looped around the tongue base and hyoid in pre-suspension and fixation by the present invention.

FIG. 24 is a cross-section of the patient 240 with the suture 38 looped around the tongue base and hyoid 250, which are now ready for suspension and fixation. As shown in FIG. 24 the suture 38 enters and exits the patient from the single entry point 244.

Figure 25:
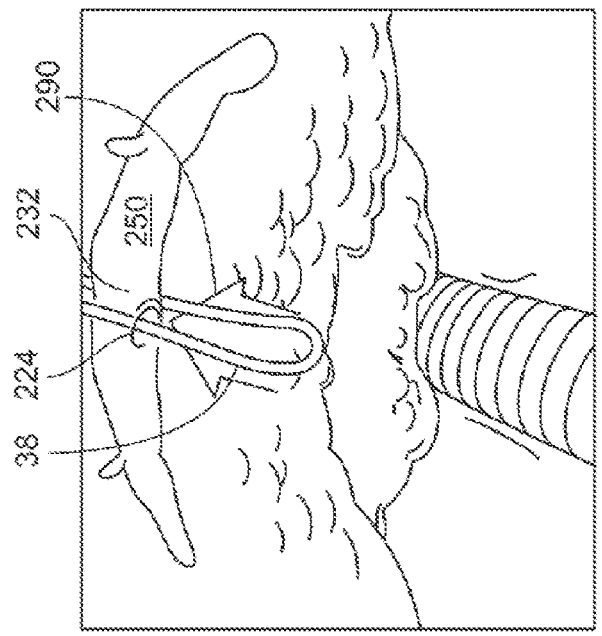
FIG. 25 is an internal view of the suture loop of FIG. 24 ready for suspension and fixation.

FIG. 25 is an internal view of the suture loop from FIG. 24 which is ready for suspension and fixation. The suture 38 is shown passing through first opening 224 on one side of hyoid bone 250 and into second opening 232 on opposite side of hyoid 250. The suture 38 is then pulled upward by medical professional as indicated by arrow 290.

Figure 26:
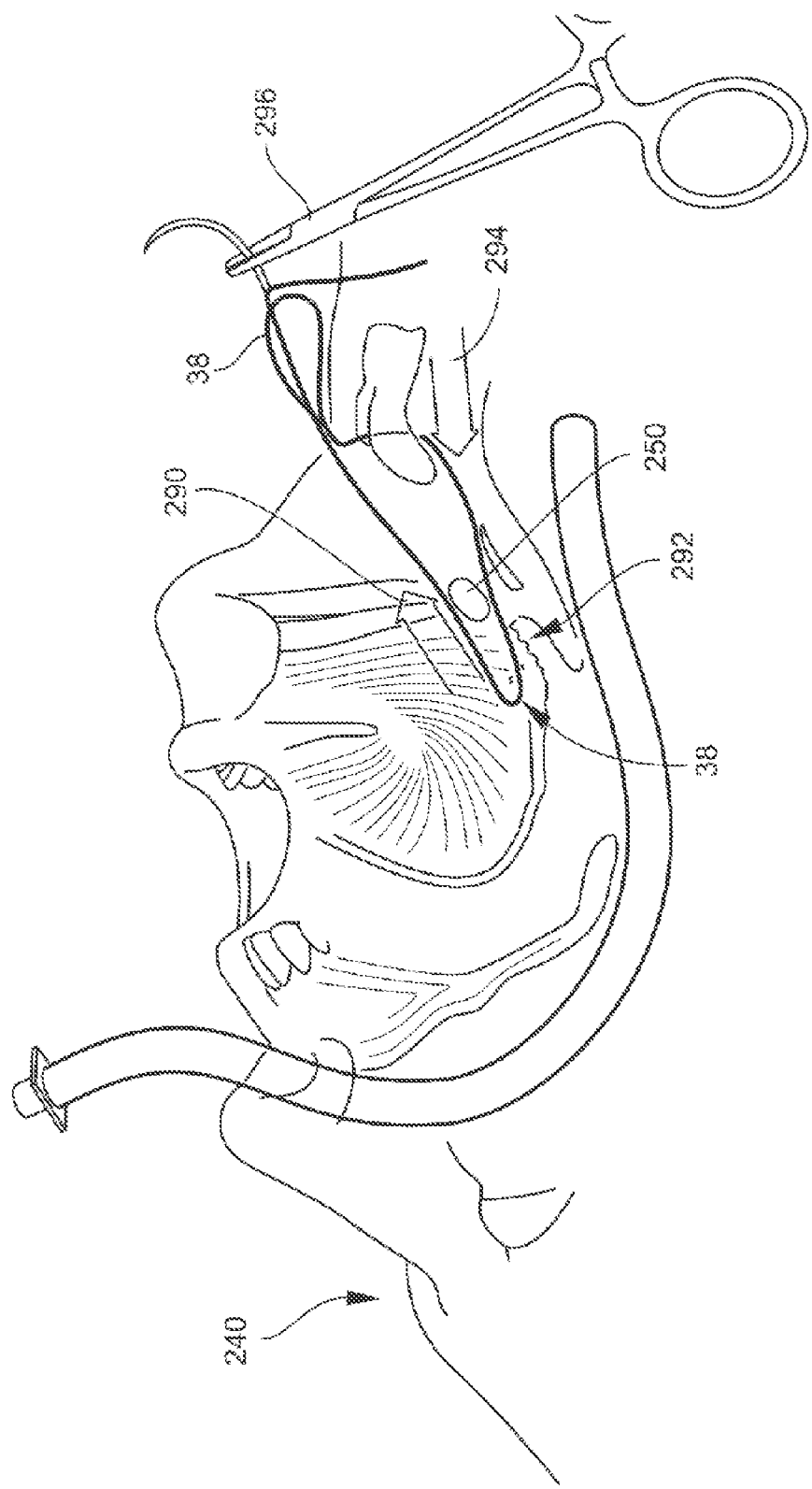
FIG. 26 is a cross section of the patient with a suture looped around tongue base and hyoid.

FIG. 26 is a cross-section of the patient 240 with the suture 38 looped around tongue base 292 and hyoid 250 which are now ready for suspension. A needle is also used for fixation of barbed suture 38 on the thyroid cartilage 294. A medical instrument 296 external to the patient's body such as a clamp, may grasp the suture ends 38 which now protrude from the patient 240 and pull the suture upward for tissue suspension as indicated by arrow 280.

Figure 27:
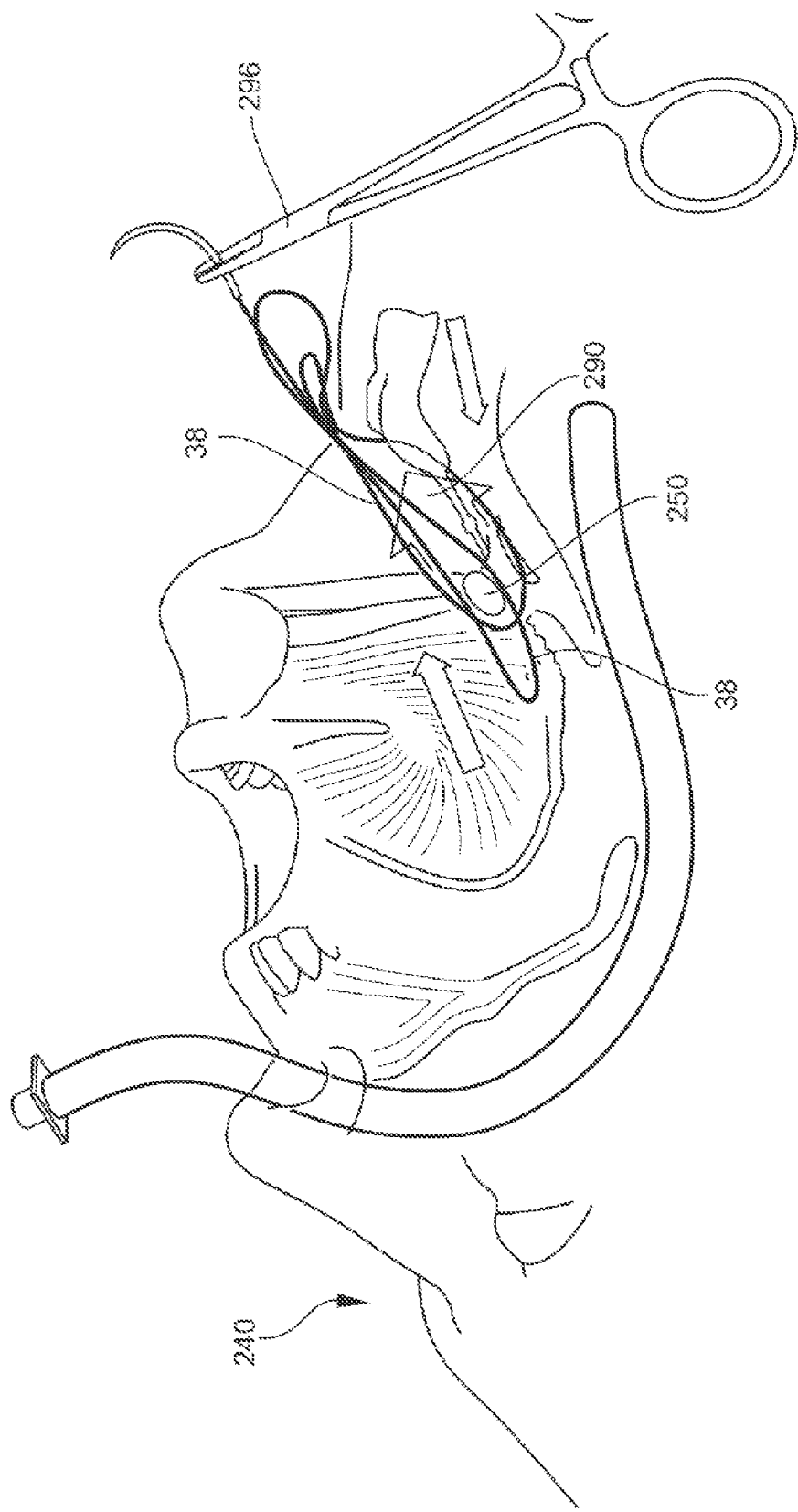
FIG. 27 is a cross section of the patient with a suture looped around the tongue base and hyoid to suspend the tongue, hyoid and thyroid.

In FIG. 27, the cross-section of the patient 240 illustrates the barbed suture 38 around tongue base and hyoid, thereby suspending the tongue, hyoid and thyroid and opening the airway of the patient. When the medical professional pulls and tightens the suture 38 in a direction away from patient (noted as arrow 290), fixation is done. This is on the thyroid cartilage.

Figure 28:
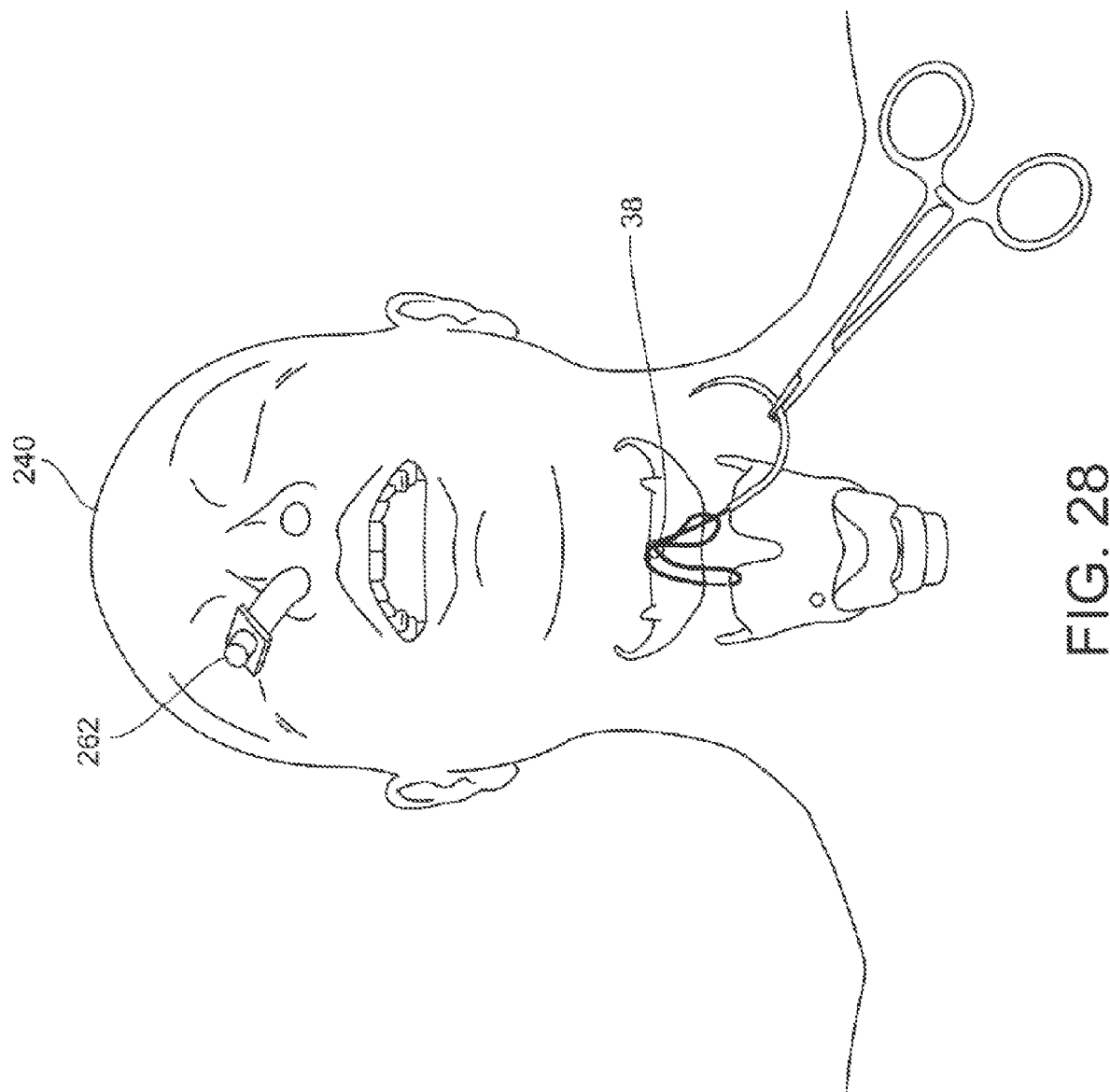
FIG. 28 is an illustration of the patient with a completed robot assisted minimally invasive suspension of the hyoid.

In FIG. 28, there is illustrated the patient 240 with the suture 38 fixed in position and tied. This is the completion of the robot-assisted minimally invasive suspension of the hyoid and tongue base so as to improve and increase a patient's airway to treat OSA.

The device and procedure of the present invention provides a minimally invasive robotic surgery for treatment of OSA which includes the suspension of the hyoid and tongue base to open the patient's airway. There are no external or internal incisions made during the procedure and the barbed sutures used are absorbable. The procedure is robotic-assisted and thereby provides an increase in visualization for the surgeon, as well as safety and accuracy of the procedure. Further, there are no permanent implants in the patient and any OSA patient with tongue collapse may benefit from the procedure. There is no AHI cut off limit and there is no need for pre-operation DISE. The procedure may be combined with other airway procedures. The use of the device and procedure has indicated that there are no adverse events or complications.

While illustrative embodiments of the invention have been described above, it is, of course, understood that many and various modifications will be apparent to those of ordinary skill in the relevant art, or may become apparent as the art develops. Such modifications are contemplated as being within the spirit and scope of the invention or inventions disclosed in this specification.

What is claimed is:

1. A method for enlarging an airway of a patient comprising:

inserting a suture passer device loaded with a suture into a patient at a first position; said patient having a neck and hyoid bone;

said first position located on the neck of said patient over said hyoid bone; said suture passer device comprising, an elongated static needle like single unitary instrument having a body with an external surface, a first end received by a handle section and a second end with a needle tip; said single unitary instrument having a head section angled away from a central axis of said body of said single unitary instrument at a first angle, and said single unitary instrument having a second angle of 18 to 22 degrees on said single unitary instrument between said body of said single unitary instrument and said head section; said body and said head section formed together as one piece;

said single unitary instrument having an insertion hook for securing said suture for insertion and an extraction hook for securing said suture during extraction; said insertion hook and said extraction hook located within said body of said single unitary instrument;

said insertion hook and said extraction hook defined by an open mouth area located between said insertion hook and said extraction hook, and an internal surface extending from the external surface of the body adjacent to said insertion hook to said external surface of the body adjacent to said extraction hook to form an opening in the body of said suture passer device which receives the suture when said suture is placed into said mouth area between said insertion hook and said extraction hook; said insertion hook and said extraction hook positioned on said body within said second angle;

said insertion hook securing said suture for delivering an insertion of said suture by said single unitary instrument and said extraction hook securing said suture for extraction of said suture by said single unitary instrument;

said suture loaded on said suture passer device on and under said insertion hook; said needle tip of said suture passer device loaded with said suture piercing tissue inside said patient to create a first opening;

extending said suture passer device with said suture on said insertion hook through said first opening and passing said suture over said hyoid bone and into a throat cavity and airway of said patient;

releasing said suture from said insertion hook of said suture passer device by use of forceps of a robotic system grasping said suture and releasing said suture from said suture passer;

removing said suture passer device through said first opening;

moving said needle tip of said suture passer device to a second position under said hyoid bone;

inserting said suture passer device through a second tissue location to create a second opening, with said extraction hook extending through said second opening;

reloading said suture onto said suture passer device on and under said extraction hook by said forceps of said robotic system loading said suture on said extraction hook;

extracting said suture passer device with said suture through said second opening to form a suture loop extending from said first opening through said second opening, said suture loop looping around said hyoid bone;

pulling said suture loop upward through said first and second opening to suspend said tissue upward and enlarge said throat cavity and said airway of the patient;

fixing said suture externally on said neck of said patient.

2. The method according to claim 1 wherein said suture is a barbed suture.

3. The method according to claim 2 wherein said barbed suture is a No. 2 barbed suture.

4. The method according to claim 1 further comprising suspending the hyoid bone of the patient and thereby opening the airway of said patient.

5. The method according to claim 4 wherein suspending the hyoid bone includes suspension of epiglottis tissue.

6. The method according to claim 1 further comprising suspending tongue base tissue of the patient and thereby opening the airway of said patient.

7. The method according to claim 6 wherein suspending the tongue base tissue includes suspension of epiglottis tissue.

8. The method according to claim 1 further comprising suspending thyroid of the patient and thereby opening the airway of said patient.

9. The method according to claim 1 wherein suspension of tissue is accomplished by a barbed suture composed of an absorbable material.

10. The method according to claim 1 wherein said insertion hook of said suture passer device is located on said single unitary instrument at a position proximal to said handle section relative to said extraction hook.

11. The method according to claim 1 wherein said body of said single unitary instrument of said suture passer device has a cylindrical shape.

12. The method according to claim 1 wherein said body of said single unitary instrument of said suture passer device has an oval shape.

13. The method according to claim 1 wherein said suture passer device is used in procedures of robotic assisted minimally invasive suspension of a hyoid.

14. The method according to claim 1 wherein said suture passer device is used in procedures with a camera.

15. The method according to claim 1 wherein said needle tip extends past a patient's epiglottis after piercing said tissue inside said patient to create said first opening.

16. The method according to claim 1 wherein said step of extending said suture passer device with said suture on said insertion hook through said first opening and passing said suture over said hyoid bone further includes extending said suture passer device over a lingual tonsil area in said first position and said step of moving said needle tip is behind said lingual tonsil area in said second position.

17. The method according to claim 1 wherein said suture is an implant.

18. The method according to claim 17 wherein said implant is a barbed implant.

19. The method according to claim 18 wherein said barbed implant is a barbed suture.

20. The method according to claim 19 wherein said barbed suture is a bidirectional barbed suture.

21. The method according to claim 18 wherein said barbed implant is a shaped barbed implant.

22. The method according to claim 18 wherein said barbed implant is absorbable.

23. The method according to claim 17 wherein said implant is a suture like device.

24. The method according to claim 1 wherein said suture passer device has at least one of said insertion hook or said extraction hook marked for visual aid.

* * * * *